(12) United States Patent
Celedon et al.

(10) Patent No.: US 11,371,986 B2
(45) Date of Patent: Jun. 28, 2022

(54) DETECTION UNITS AND METHODS FOR DETECTING A TARGET ANALYTE

(71) Applicant: Scanogen Inc., Baltimore, MD (US)

(72) Inventors: Alfredo A. Celedon, Columbia, MD (US); Joseph P. Russell, Odenton, MD (US)

(73) Assignee: SCANOGEN INC., Baltimore, MD (US)

( * ) Notice: Subject to any disclaimer, the term of this patent is extended or adjusted under 35 U.S.C. 154(b) by 520 days.

(21) Appl. No.: 16/420,231

(22) Filed: May 23, 2019

(65) Prior Publication Data

US 2019/0361016 A1 Nov. 28, 2019

Related U.S. Application Data

(60) Provisional application No. 62/676,439, filed on May 25, 2018.

(51) Int. Cl.
*G01N 33/543* (2006.01)

(52) U.S. Cl.
CPC . *G01N 33/54306* (2013.01); *G01N 33/54313* (2013.01); *G01N 33/54393* (2013.01)

(58) Field of Classification Search
CPC ....... G01N 33/54306; G01N 33/54313; G01N 33/54393; G01N 33/542; G01N 33/54326; C12N 15/1013
See application file for complete search history.

(56) References Cited

U.S. PATENT DOCUMENTS

| 5,525,468 | A | * | 6/1996 | McSwiggen | ......... | C07K 14/005 |
| | | | | | | 435/6.11 |
| 9,040,287 | B2 | * | 5/2015 | Chang | ................. | C12Q 1/6818 |
| | | | | | | 435/287.2 |

| 2015/0275215 | A1 | | 10/2015 | Cerchia et al. |
| 2016/0076083 | A1 | * | 3/2016 | Ellington ............. C12Q 1/6844 506/9 |
| 2016/0258003 | A1 | | 9/2016 | Celedon et al. |
| 2016/0304943 | A1 | * | 10/2016 | Isgut ................ C12Q 2525/301 |

FOREIGN PATENT DOCUMENTS

| WO | WO 2000/046357 A1 | 8/2000 |
| WO | WO 2011/045570 A2 | 4/2011 |
| WO | WO 2019/226841 A1 | 11/2019 |

OTHER PUBLICATIONS

International Search Report from International Application No. PCT/US2019/033645 dated Aug. 15, 2019, application now published as International Publication No. WO2019/226841 published as Nov. 28, 2019.

* cited by examiner

*Primary Examiner* — Narayan K Bhat

(74) *Attorney, Agent, or Firm* — McDermott Will and Emery LLP; Judy M. Mohr; Brett A. Schweers

(57) ABSTRACT

The present application relates to detection units and methods for detecting one or more target analytes in a sample using a complex formed by a target and first and second probes, wherein the first probe is coupled to a detectable piece, the target is coupled to the first probe and the second probe, and the second probe is coupled to a solid support. Specific binding of the detectable piece to the target analyte can be distinguished from non-specific binding of the detectable piece by measuring the number of detectable pieces that leave their initial location after exposure to a disruptor that uncouples the detectable piece from the solid support.

21 Claims, 6 Drawing Sheets

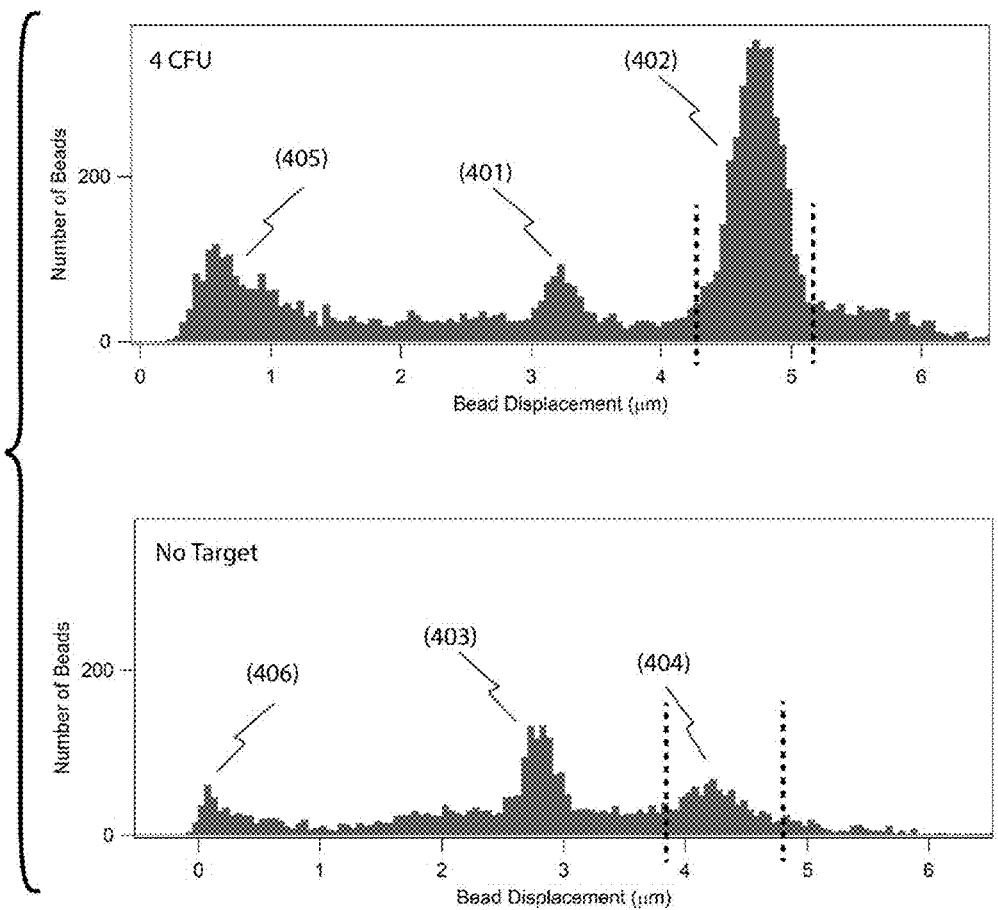

DETECTION UNITS AND METHODS FOR DETECTING A TARGET ANALYTE

CROSS-REFERENCE TO RELATED APPLICATIONS

The present applications claims the benefit of U.S. Provisional Application No. 62/676,439 filed May 25, 2018, the contents of which are incorporated by reference herein in its entirety.

STATEMENT REGARDING FEDERALLY SPONSORED RESEARCH OR DEVELOPMENT

This invention was made with government support under Grants No. R44AI122527, R43AG056208 and R43AI124871 awarded by the National Institutes of Health. The U.S. government has certain rights in the invention.

FIELD OF THE INVENTION

The present invention relates generally to detection units and methods for detecting a target analyte such as natural, synthetic, modified or unmodified nucleic acids or proteins in a sample.

BACKGROUND OF THE INVENTION

Many detection systems for determining the presence or absence of a particular target analyte in a sample are known. Examples of detection systems for detecting analytes include immunoassays, such as an enzyme linked immunosorbent assays (ELISAs), which are used in numerous diagnostic, research and screening applications. Generally, these detection systems detect the target analyte when it binds to a specific binding agent or probe resulting in a measurable signal.

When using known detection systems, such as immunoassays, the ability to detect a target analyte is often limited by the low concentration of the target analyte in the sample and by non-specific interactions, such as non-specific binding of signal producing molecules and non-specific binding of sample molecules. The ability to detect a target analyte in a biological sample is often limited by these two factors.

The signal generated by detection systems is normally proportional to the number of target analytes that bind to the specific binding probe. Therefore, when the concentration of target is low, the signal is low. The total signal can be increased by increasing the signal associated with each bound target analyte. Often, detection systems use a solid support and reporter markers, such as fluorescent molecules, to generate the signal. Several strategies that use reporter markers have been designed to increase the signal associated with each bound target, such as in branched-DNA (Hendricks et al., Am J Clin Pathol. 1995, 104(5):537) and hybrid capture (WO 2003078966 A2). While these strategies increase the total signal, they often also increase the background noise resulting from the non-specific interaction between the reporter marker and the solid support. These strategies do not offer an effective method of discriminating reporter markers non-specifically bound to the solid support.

The use of micrometer scale particles as reporter markers, described in PCT/GB2010/001913, offers a method to remove particles non-specifically bound to the solid support by applying a controlled fluid drag force on the particles.

Another strategy, disclosed in PCT/GB2010/001913 (WO 2011/045570 A2), uses a magnetic bead tethered to a solid support by an elongated molecule as a sensing apparatus to detect, for example a signal from an ELISA assay. According to this disclosure, reporter molecules are cleaved off the probes that bind to the target molecule on the substrate. The signal is amplified by releasing manipulating agents that act on an elongated molecule that tethers a bead to the solid support in a separate compartment. The bead is tethered to the solid support independently of the presence or absence of the target analyte.

Accordingly, there is a need for detection units as well as methods capable of detecting low concentrations of target analytes while distinguishing non-specific binding from specific binding in the sample.

SUMMARY OF THE INVENTION

In one aspect, the present invention provides a method of detecting a target analyte in a sample, the method comprising:
 a) providing at least one detectable piece coupled to a solid support via a complex formed by the target analyte and a first and a second probe, wherein:
  i) the first probe is coupled to the detectable piece and bound to said analyte if present, and
  ii) the second probe is coupled to the solid support and bound to said analyte if present, so that only if the target analyte is present in the sample, the detectable piece is directly or indirectly coupled to the solid support at an initial location via the complex, wherein the complex comprises an elongated region that is at least 100 nanometers in length;
 b) either applying a force to the detectable piece and measuring the displacement of the detectable piece or measuring the amount of Brownian motion of the detectable piece;
 c) exposing the complex to a disruptor that is capable of uncoupling the detectable piece from the solid support;
 d) optionally applying a force to the detectable piece; and
 e) detecting if the detectable piece has left its initial location;
 wherein the presence of the target in the sample is indicated by detectable pieces that: i) suffer a displacement or Brownian motion within a pre-determined range and ii) leave their initial location.

In another aspect, the present invention provides a method of detecting a target analyte in a sample, the method comprising:
 a) providing at least one detectable piece coupled to a solid support via a complex formed by the target analyte and a first and a second probe, wherein:
  i) the first probe is coupled to the detectable piece and bound to said analyte if present, and
  ii) the second probe is coupled to the solid support and bound to said analyte if present, so that only if the target analyte is present in the sample, the detectable piece is directly or indirectly coupled to the solid support at an initial location via the complex,
 b) optionally detecting the presence of the detectable piece;
 c) exposing the complex to a disruptor that is capable of uncoupling the detectable piece from the solid support, wherein the disruptor comprises a strand-displacement molecule capable of dissociating one or more nucleic acid duplexes formed between the target and a probe, or the disruptor comprises a degradation molecule capable of breaking one or more covalent bonds of the target analyte;
 d) optionally applying a force to the detectable piece; and
 e) detecting if any of the detectable pieces have left their initial location;

wherein a detectable piece that is indirectly bound to the analyte is likely to leave their initial location, whereas a detectable piece that is not indirectly bound to the analyte is unlikely to leave their initial location.

BRIEF DESCRIPTION OF THE FIGURES

FIG. 4A and FIG. 4B show the results of the experiment described in Example 1.

DETAILED DESCRIPTION OF THE INVENTION

Figure 1:
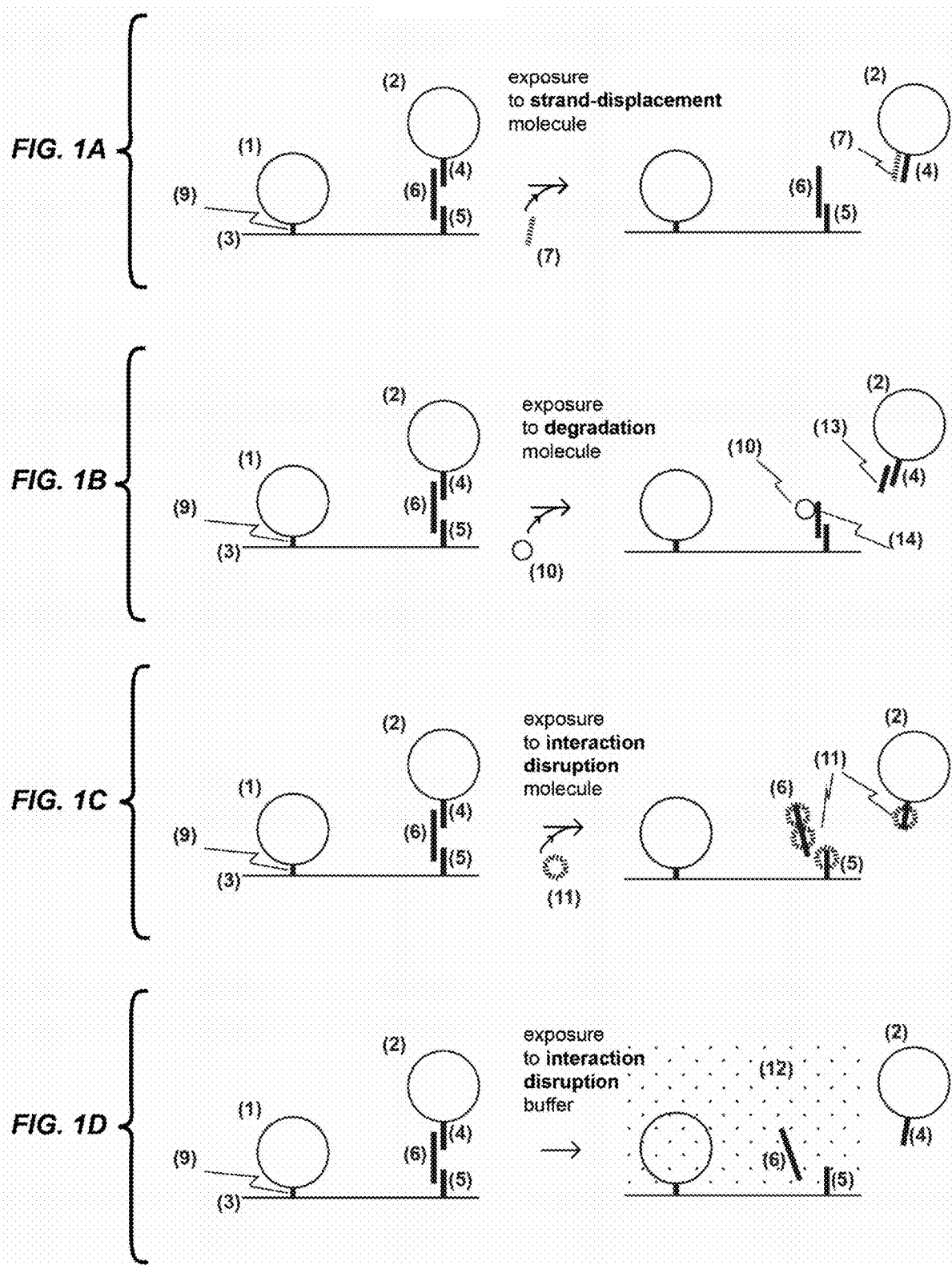
FIG. 1A depicts a solid support (3) with two detectable pieces linked to it. Detectable piece (1) is linked to the solid support via a non-specific attachment (9) which is an attachment that takes place without the intervention of the target analyte. Detectable piece (2) is linked to the solid support via a complex formed from: i) a first probe (4) coupled to the detectable piece (2) and bound to the target analyte (6) and ii) a second probe (5) coupled to the solid support (3) and to the target analyte (6). Detectable piece (2) is indirectly coupled to the solid support at an initial location. Exposure to a strand-displacement molecule (7) that binds to the first probe (4) disrupts the bond between the first probe and the target analyte. As a result, detectable piece (2) is not linked to the solid support and can move away from its initial location by Brownian motion or by the application of a force. The fact that detectable piece (1) does not leave its initial location indicates that it is not specifically attached to the solid support. The fact that detectable piece (2) leaves its initial location indicates that the target analyte is present in the sample.
FIG. 1B depicts a solid support (3) with two detectable pieces linked to it. Detectable piece (1) is linked to the solid support via a non-specific attachment (9). Detectable piece (2) is linked to the solid support via a complex formed from: i) a first probe (4) coupled to the detectable piece (2) and bound to the target analyte (6) and ii) a second probe (5) coupled to the solid support (3) and to the target analyte (6). Detectable piece (2) is indirectly coupled to the solid support at an initial location. Exposure to a degradation molecule (10) breaks one or more bonds in the target analyte dividing the original target molecule (6) into a first fragment (13) and a second fragment (14). As a result, detectable piece (2) is not linked to the solid support and can move away from its initial location by Brownian motion or by the application of a force. The fact that detectable piece (1) does not leave its initial location indicates that its attachment to the solid support is non-specific. The fact that detectable piece (2) leaves its initial location indicates that the target analyte is present in the sample.
FIG. 1C depicts a solid support (3) with two detectable pieces linked to it. Detectable piece (1) is linked to the solid support via a non-specific attachment (9). Detectable piece (2) is linked to the solid support via a complex formed from: i) a first probe (4) coupled to the detectable piece (2) and bound to the target analyte (6) and ii) a second probe (5) coupled to the solid support (3) and to the target analyte (6). Detectable piece (2) is indirectly coupled to the solid support at an initial location. Exposure to an interaction disruption molecule (11) disrupts at least one of the bonds between the target analyte (6) and the first and second probes. As a result, detectable piece (2) is not linked to the solid support and can leave its initial location by Brownian motion or by the application of a force. The fact that detectable piece (1) does not leave its initial location indicates that its attachment to the solid support is non-specific. The fact that detectable piece (2) leaves its initial location indicates that the target analyte is present in the sample.
FIG. 1D depicts a solid support (3) with two detectable pieces linked to it. Detectable piece (1) is linked to the solid support via a non-specific attachment (9). Detectable piece (2) is linked to the solid support via a complex formed from: i) a first probe (4) coupled to the detectable piece (2) and bound to the target analyte (6) and ii) a second probe (5) coupled to the solid support (3) and to the target analyte (6). Detectable piece (2) is indirectly coupled to the solid support at an initial location. Exposure to an interaction disruption buffer (12) disrupts at least one of the bonds between the target analyte (6) and the first (4) and second (5) probes. As a result, detectable piece (2) is not linked to the solid support and can move away from its initial location by Brownian motion or by the application of a force. The fact that detectable piece (1) does not leave its initial location indicates that its attachment to the solid support is non-specific. The fact that detectable piece (2) leaves its initial location indicates that the target analyte is present in the sample.

It should be appreciated that the particular implementations shown and described herein are examples and are not intended to otherwise limit the scope of the application in any way.

The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The terms "about" and "substantially" are used herein to mean approximately, in the region of, roughly, or around. When the terms "about" and "substantially" are used in conjunction with a numerical range, it modifies that range by extending the boundaries above and below the numerical values set forth. In general, the terms "about" and "substantially" are used herein to modify a numerical value above and below the stated value by a variance of less than about 20%.

Technical and scientific terms used herein have the meaning commonly understood by one of skill in the art to which the present application pertains, unless otherwise defined. Reference is made herein to various methodologies and materials known to those of skill in the art. Standard reference works setting forth the general principles of recombinant DNA technology include Sambrook et al., "Molecular Cloning: A Laboratory Manual," 2nd Ed., Cold Spring Harbor Laboratory Press, New York (1989); Kaufman et al., Eds., "Handbook of Molecular and Cellular Methods in Biology in Medicine," CRC Press, Boca Raton (1995); and McPherson, Ed., "Directed Mutagenesis: A Practical Approach," IRL Press, Oxford (1991), the disclosures of each of which are incorporated by reference herein in their entireties.

The terms "target analyte" or "analyte," are used herein to denote the molecule to be detected in the test sample. According to the invention, there can be any number of different target analytes in the test sample (from one to one thousand, or even more). The target analyte can be any molecule for which there exists a naturally or artificially prepared specific binding member. Examples of target analytes include, but are not limited to, a nucleic acid, oligonucleotide, DNA, RNA, protein, peptide, polypeptide, amino acid, antibody, carbohydrate, lipid, hormone, steroid, toxin, vitamin, any drug administered for therapeutic and illicit purposes, a bacterium, a virus, cell, as well as any antigenic substances, haptens, antibodies, metabolites, water pollutants (such as nitrates, phosphates, heavy metals, etc.) and molecules having an odor, such as compounds containing sulfur and/or nitrogen, for example hydrogen sulfide, ammonia, amines, etc., and combinations thereof.

In a preferred embodiment, the target analyte is a nucleic acid. The nucleic acid can be from any source in purified or unpurified form including DNA (dsDNA and ssDNA) and RNA, including tRNA, mRNA, rRNA, siRNA, mitochondrial DNA and RNA, chloroplast DNA and RNA, DNA-RNA hybrids, or mixtures thereof, genes, chromosomes, plasmids, the genomes of biological materials, including microorganisms such as bacteria, yeast, viruses, viroids, molds, fungi, plants, animals, humans, and fragments thereof. The nucleic acid can be single stranded DNA obtained by exposing double stranded DNA to an exonuclease enzyme, such as exonuclease III. The target analyte can be obtained from various biological materials by procedures well known in the art.

In another preferred embodiment, the target analyte is a short nucleic acid containing less than about 200 base pairs or less than about 200 nucleotides. In general, such molecules are difficult to detect using PCR-based techniques because suitable primers often cannot be found in such a short sequence. A particular case of small DNA molecules are molecules of less than about 40 nucleotides. These molecules are smaller than the combined size of standard PCR primers (each primer about 20 nucleotides). Short nucleic acid molecules are common in nature; exemplary cases are small interfering RNA (siRNA), micro-RNA (miRNA) and its precursors, pri-miRNA and pre-miRNA, and fragmented DNA molecules produced after cell death and present in blood, urine and other body fluids.

In another preferred embodiment, the target analyte is ribosomal RNA. Ribosomal ribonucleic acid (rRNA) is the RNA component of the ribosome, and is essential for protein synthesis in all living organisms. It constitutes the predominant material within the ribosome, which is approximately 60% rRNA and 40% protein by weight, or ⅗ of ribosome mass. Ribosomes contain two major rRNAs and 50 or more proteins. The ribosomal RNAs form two subunits, the large subunit (LSU) and small subunit (SSU). The LSU rRNA acts as a ribozyme, catalyzing peptide bond formation. rRNA sequences are widely used for working out evolutionary relationships among organisms, since they are of ancient origin and are found in all known forms of life.

The term "probe" is understood herein to mean a molecule or a molecular complex formed by two or more molecules that is capable of binding to the target analyte and also capable of being coupled to, depending on the context, either to a solid support or to a detectable piece. Probes have a region capable of binding to the target analyte.

The term "first probe" is understood herein to mean the probe that is capable of coupling to a detectable piece. The term "second probe" is understood herein to mean the probe that is capable of coupling to the solid support. For example, if the target analyte is a nucleic acid, oligonucleotide, DNA, or RNA, the region capable of binding the target analyte in both the first and second probe may comprise a nucleic acid, oligonucleotide, DNA, or RNA molecule having a sequence complementary to the target analyte and capable of hybridizing thereto. As another example, if the target analyte is a protein, peptide, polypeptide, or amino acid, the region capable of binding the target analyte in both the first and second probe may comprise an antibody, an antigen-binding fragment or an aptamer that specifically binds to the target analyte. Probes may comprise regions of different nature. For example, a probe may comprise three different regions: a single stranded DNA region, a double stranded DNA region and a protein region.

The terms "coupling", "to couple", "coupled", "binding" "to bind", "bound", "link", "linked", "association", "to attach" and "attachment" refer to any form of immobilization of a probe onto a surface, including covalent, non-covalent, direct, and mediated by one or more molecules. The same terms also refer to the covalent or non-covalent bonding between a probe and a target analyte. Non-covalent bonding can be formed by ionic interactions, via hydrogen bonding, etc.

The term "antibody" includes an immunoglobulin or an antigen-binding fragment thereof.

The term "antigen-binding fragment" includes a part of an antibody molecule that comprises amino acids responsible for the specific binding between antibody and antigen. For certain antigens, the antigen-binding domain or antigen-binding fragment may only bind to a part of the antigen. The part of the antigen that is specifically recognized and bound by the antibody is referred to as the "epitope" or "antigenic determinant." Antigen-binding domains and antigen-binding fragments include Fab (Fragment antigen-binding); a $F(ab')_2$ fragment, a bivalent fragment having two Fab fragments linked by a disulfide bridge at the hinge region; Fv fragment; a single chain Fv fragment (scFv) see e.g., Bird et al. (1988) *Science* 242:423-426; and Huston et al. (1988) *Proc. Natl. Acad. Sci. USA* 85:5879-5883); a Fd fragment having the two $V_H$ and $C_H1$ domains; dAb (Ward et al., (1989) *Nature* 341:544-546), and other antibody fragments that retain antigen-binding function. The Fab fragment has $V_H$-$C_H1$ and $V_L$-$C_L$ domains covalently linked by a disulfide bond between the constant regions. The F, fragment is smaller and has $V_H$ and $V_L$ domains non-covalently linked. To overcome the tendency of non-covalently linked domains to dissociate, a $scF_v$ can be constructed. The $scF_v$ contains a flexible polypeptide that links (1) the C-terminus of $V_H$ to the N-terminus of $V_L$, or (2) the C-terminus of $V_L$ to the N-terminus of $V_H$. A 15-mer $(Gly_4Ser)_3$ peptide may be used as a linker, but other linkers are known in the art. These antibody fragments are obtained using conventional techniques known to those with skill in the art, and the fragments are evaluated for function in the same manner as are intact antibodies.

The term "aptamer" includes oligonucleotide or peptide molecules that bind to a specific target molecule. Aptamers are usually created by selecting them from a large random sequence pool, but natural aptamers also exist in riboswitches. Aptamers can be used for both basic research and clinical purposes as macromolecular drugs. Aptamers can be combined with ribozymes to self-cleave in the presence of their target molecule. These compound molecules have additional research, industrial and clinical applications. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms (Molecules 2017, 22(2), 215). In the molecular level, aptamers bind to its target site through non-covalent interactions. Aptamers bind to these specific targets because of electrostatic interactions, hydrophobic interactions, and their complementary shapes. Aptamers are useful in biotechnological and therapeutic applications as they offer molecular recognition properties that rival that of the commonly used biomolecule, antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. Peptide aptamers (Nature. 380 (6574): 548) are artificial proteins selected or engineered to bind specific target molecules. These proteins consist of one or more peptide loops of variable sequence displayed by a protein scaffold. They are typically isolated from combinatorial libraries and often subsequently improved by directed mutation or rounds of variable region mutagenesis and selection. In vivo, peptide aptamers can bind cellular protein targets and exert biological effects, including interference with the normal protein interactions of their targeted molecules with other proteins.

The term "elongated region" refers to a section that may be part of the complex formed by the target analyte and the first and second probes that is sufficiently long such that when the complex tethers a detectable piece to a solid support the displacement of the detectable piece can be detected and differentiated from the displacement of particles that are non-specifically attached to the solid support. In preferred embodiments, the elongated region is a biomolecule, such as a polysaccharide, polypeptide or nucleic acid, longer than about 0.1 micrometers, preferably between about 0.3 and about 100 micrometers long. In even more preferred embodiments, the elongated region between about 1 and about 50 micrometer long.

The terms "test sample" or "sample" are used interchangeably herein and include, but are not limited to, biological samples that can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like, biological fluids such as cell culture and blood culture, fixed tissue specimens and fixed cell specimens, PCR amplification products or a purified product of one of the above samples. Additional relevant samples of the present invention are lysates of body fluids and lysates of other fluids that contain cells. In a lysate, all or some of the cells of the original fluid have been lysed. Many methods are known in the art for lysing cells, including, sample heating, surfactants, enzymes and bead beating. A "sample" may include gaseous mediums, such as ambient air, chemical or industrial intermediates, chemical or industrial products, chemical or industrial byproducts, chemical or industrial waste, exhaled vapor, internal combustion engine exhaust, or headspace vapor such as vapor surrounding foods, beverages, cosmetics, vapor surrounding plant or animal tissue and vapor surrounding a microbial sample. Another example of "sample" relevant to this invention is a liquid solution produced by dissolving material collected by filtering a gaseous sample or a liquid solution produced by exposing the liquid to a gaseous sample. Additional sample mediums include supercritical fluids such as supercritical $CO_2$ extricate. Other exemplary mediums include liquids such as water or aqueous solutions, oil or petroleum products, oil-water emulsions, liquid chemical or industrial intermediates, liquid chemical or industrial products, liquid chemical or industrial byproducts, and liquid chemical or industrial waste. Additional exemplary sample mediums include semisolid mediums such as animal or plant tissues, microbial samples, or samples containing gelatin, agar or polyacrylamide.

As used herein, a "detectable signal" which can be generated according to the invention includes, but is not limited to, an electrical, mechanical, optical, magnetic, acoustic or thermal signal. In preferred embodiments, the detectable signal is optical.

The term "solid support" is used herein to denote any solid material suitable for coupling to a probe and which is amenable to the detection methods disclosed herein. The number of possible suitable materials is large and would be readily known by one of ordinary skill in the art.

The term "detectable region" is used to indicate a region of the solid support. The "detectable region" may in some cases be the entire solid support.

The term "detectable piece" is used to indicate a structure suitable for coupling to a probe and which is amenable to the detection methods disclosed herein. The detectable piece can be directly or indirectly detected. Examples of "detectable piece" of importance for the present invention include a particle, fluorescent particle, fluorescent molecule, and enzymes that catalyze the formation of a detectable molecule, such as horseradish peroxidase and alkaline phosphatase.

The term "disruptor" is used to indicate a molecule, a buffer, combinations thereof, or other chemical agents that alone or in combination with other conditions can uncouple a detectable piece from the solid support that is coupled to the solid support via a target complex. Preferably, the disruptor will uncouple to a lesser extent a detectable piece that is coupled to the solid support without participation of the target analyte.

The association of the target and the first probe and the second probe forms a "complex" or "target complex". The detectable piece can be indirectly coupled to the solid support via a target complex. The disruptor disrupts a target complex when the complex is broken up in two or more parts such that it is not able to couple a detectable piece to the solid support and/or when the coupling of the first probe to the detectable piece is broken and/or when the coupling of the second probe to the solid support is broken. In preferred embodiments, the disruptor action requires the presence of the target.

Examples of disruptor buffers are buffers where non-covalent attractions between molecules are reduced and buffers where electrostatic repulsions are increased. Important examples of disruptor buffers are buffers with low salt, in which electrostatic repulsion increases, buffers with high salt, in which ionic attraction is reduced, high pH buffers, and organic solvents.

The term "degradation molecule" is used herein to indicate a disruptor that breaks one or more covalent bonds.

The term "degradation" is used to indicate a process where one or more covalent bonds are broken.

In preferred embodiments, the disruptor is a degradation molecule. Disruptors of this type are abundant and known to someone skilled in the art. Important examples are nucleases and proteases. The phosphodiester bonds of nucleic acids can be broken using a nuclease enzyme. Nucleases can generate single and double stranded breaks in their target molecules. In living organisms, they are essential machinery for many aspects of DNA repair. Nucleases are also extensively used in molecular cloning. There are two primary classifications based on the locus of activity. Exonucleases digest nucleic acids from the ends. Endonucleases act on regions in the middle of target molecules. They are further subcategorized as deoxyribonucleases and ribonucleases. The former acts on DNA, the latter on RNA. Important examples of enzymes that act on RNA include: RNase H, RNase A, RNase III, RNase L, RNase P, RNase PhyM, RNase T1, RNase T2, RNase U2, or RNase V. Important examples for this application of enzymes that act on DNA include restriction endonucleases and nicking endonucleases. The peptide bonds of proteins and polypeptides can be broken using a protease. Some proteases detach the terminal amino acids from the protein chain (exopeptidases, such as aminopeptidases, carboxypeptidase A); others attack internal peptide bonds of a protein (endopeptidases, such as trypsin, chymotrypsin, pepsin, papain, elastase). Proteolysis can be highly promiscuous such that a wide range of protein substrates are hydrolysed. This is the case for digestive enzymes such as trypsin. Promiscuous proteases typically bind to a single amino acid on the substrate and so only have specificity for that residue. For example, trypsin is specific for the sequences . . . KV\ . . . or . . . RV\ . . . ('\'=cleavage site). Proteinase K is a broad-spectrum serine protease. The predominant site of cleavage is the peptide bond adjacent to the carboxyl group of aliphatic and aromatic amino acids with blocked alpha amino groups. It is commonly used for its broad specificity. Conversely, some proteases are highly specific and only cleave substrates with a certain sequence. Blood clotting (such as thrombin) and viral polyprotein processing (such as TEV protease) requires this level of specificity in order to achieve precise cleavage events. This is achieved by proteases having a long binding cleft or tunnel with several pockets along it which bind the specified residues. For example, TEV protease is specific for the sequence . . . ENLYFQ\S . . . ('\'=cleavage site).

In even more preferred embodiments, the disruptor is a degradation molecule that can break one or more covalent bonds of the target analyte and does not break bonds of the probes. A detectable piece that is attached to the solid support without the target analyte (non-specifically) will not be uncoupled from the solid support by this type of disruptor, while a detectable piece that is coupled to the solid support via the target complex will be readily uncoupled by this type of disruptor. Examples of this embodiment are the following: the target analyte is a protein, the probes are nucleic acid aptamers and the degradation molecule is a proteinase enzyme. In another example, the target analyte is an RNA molecule, the probes are DNA molecules and the degradation molecule is a ribonuclease enzyme.

Figure 2:
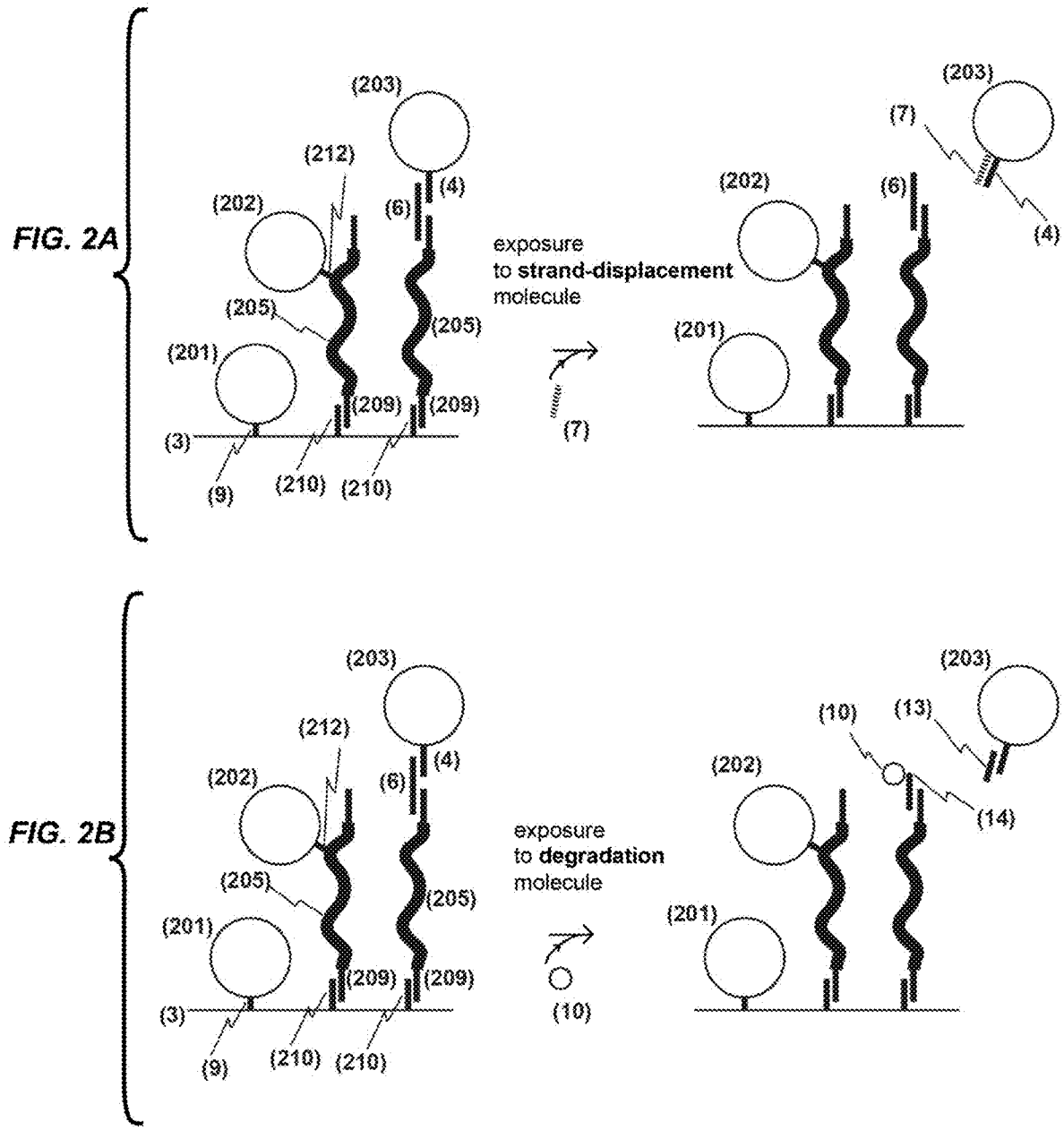
FIG. 2A depicts a solid support (3) with three detectable pieces linked to it. Detectable piece (201) is linked to the solid support via a non-specific attachment (9) to the solid support. Detectable piece (202) is linked to the solid support via a non-specific attachment (212) to the second probe which is coupled to the solid support via the interaction of region (209) with a probe (210) attached to the solid support. The second probe (205) comprises an elongated region. Detectable piece (202) is linked to the solid support without the intervention of the target analyte. Detectable piece (203) is linked to the solid support via a complex formed from: i) a first probe (4) coupled to the detectable piece (203) and bound to the target analyte (6) and ii) a second probe (205) which comprises an elongated region and is coupled to the solid support (3) and to the target analyte (6). The second probe (205) is coupled to the solid support via the interaction of region (209) with a probe (210) attached to the solid support. Measuring the displacement of detectable pieces (201), (202) and (203) under an external force will show that detectable piece (201) does not suffer displacement, indicating that detectable piece (201) is non-specifically attached to the solid support. However, it may not be possible to differentiate the displacement of detectable piece (202) and detectable piece (203) and therefore, it may not be possible to detect that detectable piece (202) is non-specifically attached. Exposure to a strand-displacement molecule (7) that binds to the first probe (4) disrupts the bond between the first probe and the target analyte (it will be recognized that the strand-displacement molecule (7) may also bind to other locations within the complex (not shown) with the effect of releasing detectable piece (203) from solid support (3)). As a result, detectable piece (203) is not linked to the solid support and leaves its initial location by Brownian motion or by the application of a force. The fact that detectable piece (202) remains tethered to the solid support indicates that its attachment is non-specific. The fact that detectable piece (203) leaves its initial location indicates that the target analyte is present in the sample.
FIG. 2B depicts a solid support (3) with three detectable pieces linked to it as in FIG. 2A. Exposure to a degradation molecule (10) breaks one or more bonds in the target analyte dividing the original target molecule (6) into a first fragment (13) and a second fragment (14). As a result, detectable piece (203) is not linked to the solid support and leaves its initial location by Brownian motion or by the application of a force. The fact that detectable piece (202) remains tethered to the solid support indicates that its attachment is non-specific. The fact that detectable piece (203) leaves its initial location indicates that the target analyte is present in the sample.

FIG. 1B and FIG. 2B show examples of embodiments of the present invention where the disruptor breaks one or more bonds within the target analyte. FIG. 1B depicts a solid support (3) with two detectable pieces linked to it. Detectable piece (1) is linked to the solid support via a non-specific attachment (9). Detectable piece (2) is linked to the solid support via a complex formed from: i) a first probe (4) coupled to the detectable piece (2) and bound to the target analyte (6) and ii) a second probe (5) coupled to the solid support (3) and to the target analyte (6). Detectable piece (2) is indirectly coupled to the solid support at an initial location. Exposure to a degradation molecule (10) breaks one or more bonds in the target analyte dividing the original target molecule (6) into a first fragment (13) and a second fragment (14). As a result, detectable piece (2) is not linked to the solid support and can leave its initial location by Brownian motion or by the application of a force. The fact that detectable piece (1) does not leave its initial location indicates that its attachment to the solid support is non-specific. The fact that detectable piece (2) leaves its initial location indicates that the target analyte is present in the sample.

FIG. 2B depicts a solid support (3) with three detectable pieces linked to it. Detectable piece (201) is linked to the solid support via a non-specific attachment (9) to the solid support. Detectable piece (202) is linked to the solid support via a non-specific attachment (212) to the second probe which is coupled to the solid support via the interaction of region (209) with a probe (210) attached to the solid support. The second probe (205) comprises an elongated region. Detectable piece (202) is linked to the solid support without the intervention of the target analyte. Detectable piece (203) is linked to the solid support via a complex formed from: i) a first probe (4) coupled to the detectable piece (203) and bound to the target analyte (6) and ii) a second probe (205) which comprises an elongated region and is coupled to the solid support (3) and to the target analyte (6). The second probe (205) is coupled to the solid support via the interaction of region (209) with a probe (210) attached to the solid support. Measuring the displacement of detectable piece (201), (202) and (203) under an external force will show that detectable piece (201) does not suffer displacement, indicating that detectable piece (201) is non-specifically attached to the solid support. However, it may not be possible to differentiate the displacement of detectable piece (202) and detectable piece (203) and therefore, it may not be possible to detect that detectable piece (202) is non-specifically attached. Exposure to a degradation molecule (10) breaks one or more bonds in the target analyte dividing the original target molecule (6) into a first fragment (13) and a second fragment (14). As a result, detectable piece (203) is not linked to the solid support and can move away from its initial location by Brownian motion or by the application of a force. The fact that detectable piece (202) remains tethered indicates that its attachment is non-specific. The fact that detectable piece (203) leaves its initial location indicates that the target analyte is present in the sample.

In other preferred embodiments, the disruptor is a molecule that breaks non-covalent interactions. Examples of these disruptors are strand-displacement molecules.

Figure 3:
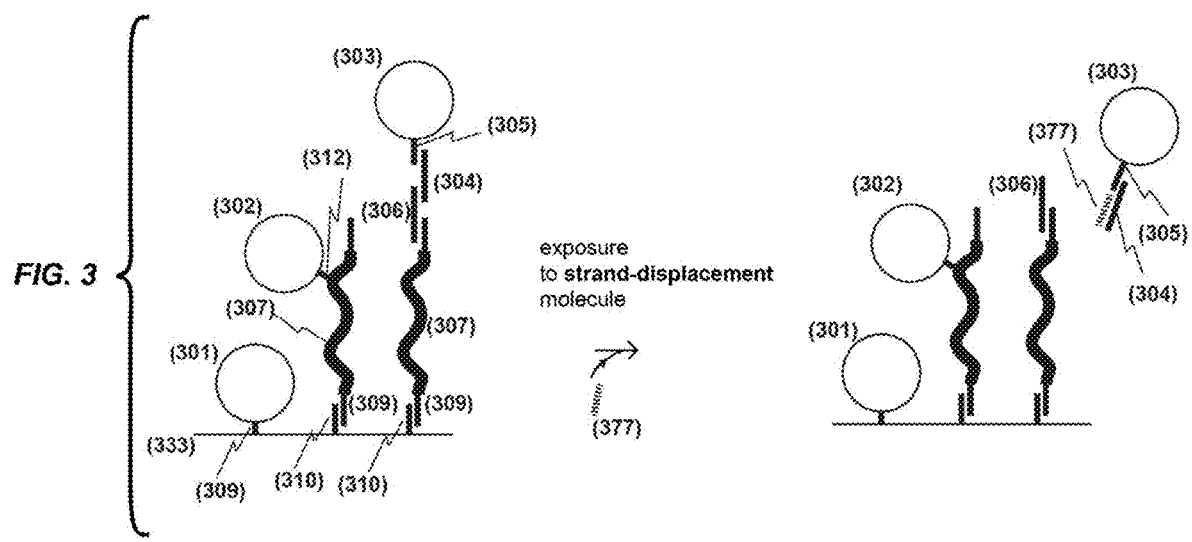
FIG. 3 depicts the experiment described in Example 1.

A "strand-displacement" disruptor molecule is a nucleic acid that alone or in combination with other conditions denature a nucleic acid duplex involved in coupling the detectable piece to the solid support by hybridizing to one of the strands in the duplex. This type of reaction between nucleic acids is known as "strand displacement" (Zhang and Winfree, J. Am. Chem. Soc. 2009, 131, 17303). In a strand displacement reaction, a duplex formed by nucleic acid strands S1 and S2 is disrupted by a strand-displacement nucleic acid S3 that is complementary to S1. In most cases, S1 has a short single-stranded region, known as a toehold, that is not part of the nucleic acid duplex being disrupted (the toehold does not hybridize to S2). In most cases, during a strand displacement reaction S3 hybridizes first to the toehold in S1 and then proceeds to hybridize to the rest of S1. The presence of the toehold significantly accelerates the strand displacement reaction. Examples of how strand-displacement nucleic acids can be used in this invention are described below. The bond between the target analyte and the first and/or the second probe may be broken using a strand displacement reaction. The strand-displacement molecule used in this reaction may hybridize to the target, to the first probe or to the second probe and disrupts the duplex formed by the target with one or both probes. FIG. 1A, FIG. 2A and FIG. 3 show examples where the strand-displacement molecule hybridizes to the first probe breaking the bond between the first probe and the target analyte. The sequence specificity of the assay can be increased using strand-displacement disruptors that hybridize to the target and use a toehold in the target molecule. Only target-probe duplexes formed by targets that have the toehold sequence will be disrupted. Another example of strand-displacement disruptors are disruptors that disrupt the coupling between the first probe and the detectable piece. For example, the first probe and a molecule M which is immobilized to the detectable piece form a duplex and this nucleic acid duplex can be disrupted by strand displacement. In this case, the strand-displacement molecule can hybridize to the first probe or to molecule M. In any strand displacement reaction, the strand-displacement molecule does not need to hybridize to the full region participating in the duplex to be disruptive, instead, it may only need to displace enough of one of the strands, so that the remainder of the duplex is unstable and denatures. In preferred embodiments, the strand-displacement disruptor hybridizes to the target analyte and disrupts the interaction with the first and/or the second probe, so that it specifically uncouples detectable pieces that are coupled via the target analyte. In other preferred embodiments, the strand-displacement disruptor hybridizes to the first or to the second probe and disrupts the interaction of the first or second probe with the target analyte.

Other examples of disruptors that break non-covalent interactions are molecules that disrupt non-covalent interactions of molecules in water including electrostatic interactions, such as hydrogen bonding, π-effects, van der Waals forces and hydrophobic effects. This type of disruptor molecule may directly break the interaction between two molecules or denature one or both of the molecules which leads to their dissociation. An important type of disruptor in this category are chaotropic agents. A chaotropic agent is a molecule in water solution that can disrupt the hydrogen bonding network between water molecules (i.e. exerts chaotropic activity). This has an effect on the stability of the native state of other molecules in the solution, mainly macromolecules (e.g., proteins and nucleic acids) by weakening the hydrophobic effect. For example, a chaotropic agent reduces the amount of order in the structure of a protein formed by water molecules, both in the bulk and the hydration shells around hydrophobic amino acids and may cause its denaturation. Common chaotropic agents of importance for this invention include n-butanol, ethanol, guanidinium chloride, lithium perchlorate, lithium acetate, magnesium chloride, phenol, 2-propanol, sodium dodecyl sulfate, thiourea, formamide and urea.

In an embodiment of the present invention, two or more target analytes are detected. According to this embodiment, a different combination of first and second probe is used for each target analyte, wherein each target forms a different complex with the probes that bind to it. One or more disruptors are used, wherein each of these disruptors disrupts the target complex of one or more target analytes. If two or more disruptors are used, they can be put in contact with the target complexes simultaneously (all of them at the same time), or in a sequential manner (one or more at a time). The detectable pieces on the solid support are monitored as each of the disruptors is used. The detectable pieces that leave their location during exposure to a disruptor are indicative of the presence of the probe-target complex that the disruptor is capable of disrupting.

In an example of this embodiment, two or more strand-displacement disruptors are used to detect multiple target analytes in the present invention. The target complexes are exposed to groups of one or more strand-displacement disruptors in a sequential manner and the number of detectable pieces that leave their initial location after exposure to each group of disruptors is determined.

The term "surface" or "surfaces" is used to indicate the external layer of the solid support and the particles. In exemplary embodiments, the solid support or the particles may be composed of modified or functionalized glasses, inorganic glasses, plastics, including acrylics, polystyrene and copolymers of styrene, polypropylene, polyethylene, polybutylene, polyurethanes, Teflon, polysaccharides, nylon or nitrocellulose, resins, and other polymers, carbon, metals, ceramics, silica or silica-based materials including silicon and modified silicon and silicon wafers. In aspects, the surface can be a composite material.

Surfaces can be functionalized with molecules by physical or chemical adsorption. In preferred embodiments, the surfaces are functionalized with probes or with molecules capable of coupling to probes. Such methods of functionalization are known in the art. For instance, a gold surface can be functionalized with nucleic acids that have been modified with alkanethiols at their 3'-termini or 5'-termini. See, for example, Whitesides, Proceedings of the Robert A. Welch Foundation 39th Conference On Chemical Research Nanophase Chemistry, Houston, Tex., pages 109-121 (1995). See also Mucic et al., Chem. Commun. 555-557 (1996) (describes a method of attaching 3' thiol DNA to flat gold surfaces; this method can be used to attach oligonucleotides to nanoparticles). The alkanethiol method can also be used to attach oligonucleotides to other metal and semiconductors. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, Chemical Technology, 4, 370-377 (1974) and Matteucci and Caruthers, J. Am. Chem. Soc., 103, 3185-3191 (1981) for binding of oligonucleotides to silica and glass surfaces, and Grabar et al., Anal. Chem., 67, 735-743 for binding of aminoalkylsiloxanes and for similar binding of mercaptoaklylsiloxanes)-. Oligonucleotides terminated with a 5' thionucleoside or a 3' thionucleoside may also be used for attaching oligonucleotides to solid surfaces. Another example of surface functionalization that is important for the present invention is the immobilization of antibodies and other binding members to the surface either by physical adsorption or by direct or indirect chemical linkage. For instance, surfaces can be functionalized by chemically linking streptavidin molecules to them, which are capable of coupling to probes comprising one or more biotin molecules. The following reference describes the attachment of biotin labeled oligonucleotides to a streptavidin functionalized surface. Shaiu et al., Nucleic Acids Research, 21, 99 (1993). Digoxigenin and anti-Digoxigenin antibodies can also be used to attach probes to surfaces.

The surfaces can be functionalized by a monolayer of one or more molecules. Methods of producing self-assembled monolayers are well known in the art. In particular, there are several known methods to assemble monolayers of thiolates on metal surfaces. See e.g., Love, J. C. et al., Chem. Rev., 105, 1103 (2005).

The surface functionalization methods described above can be used to couple molecules that prevent or reduce non-specific interactions with the surface. For instance, after immobilization on to the surface of an analyte binding molecule, such as a ssDNA or an antibody, physical adsorption on the surface of a protein that blocks non-specific interactions is often conducted. Common proteins used as blockers are: bovine serum albumin (BSA), fish serum and milk proteins, such as casein.

The following references describe other methods that may be employed to attach oligonucleotides to surfaces: Nuzzo et al., J. Am. Chem. Soc., 109, 2358 (1987) (disulfides on gold); Allara and Nuzzo, Langmuir, 1, 45 (1985) (carboxylic acids on aluminum); Allara and Tompkins, J. Colloid Interface Sci., 49, 410-421 (1974) (carboxylic acids on copper); Iler, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Acc. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 1034 (1987) (silanes on silica); Wasserman et al., Langmuir, 5, 1074 (1989) (silanes on silica); Eltekova and Eltekov, Langrnuir, 3, 951 (1987) (aromatic carboxylic acids, aldehydes, alcohols and methoxy groups on titanium dioxide and silica); Lec et al., J. Phys. Chem., 92, 2597 (1988) (rigid phosphates on metals).

Glass and other materials can be functionalized with a silane aldehyde, Triethoxysilylundecanal and the aldehyde-modified glass surface can then covalently bind amino-containing biomolecules (J. Mater. Chem., 2011, 21, 4384-4392; NATURE PROTOCOLS, 2006, 1, 1711-1724). Another important type of functionalization involves azides. The copper catalyzed Huisgen 1,3 cycloaddition of azides and alkynes to form 1,2,3 triazoles ("click" chemistry) has become a very popular reaction in bioconjugation over the past decades (Pharm Res. 2008 October; 25(10): 2216-2230; Drug Discov Today. 2003 Dec. 15; 8(24):1128-37). It can be performed under a wide range of conditions (temperature, pH, solvents), the reaction is fast and the resulting triazoles are very stable and formed in high yields.

As used herein, a "polymer" is a molecule formed by monomers in which each monomer is covalently linked to other monomers.

The term "monomer" is used herein to refer to a molecule that has the ability to combine with identical or other molecules in a process known as polymerization. The polymerization reaction may be a dehydration or condensation reaction (due to the formation of water ($H_2O$) as one of the products) where a hydrogen atom and a hydroxyl (—OH) group are lost to form $H_2O$ and an oxygen molecule bonds between each monomer unit.

Examples of polymers suitable for use in this invention are polyethylene oxide (PEO), polyethylene glycol (PEG), polyisopropylacrylamide (PNIPAM), polyacrylamide (PAM), polyvinyl alcohol (PVA), polyethylenimine (PEI), polyacrylic acid, polymethacrylate and polyvinylpyrrolidone (PVP) polyvinyls, polyesters, polysiloxanes, polyamides, polyurethanes, polycarbonates, fluoropolymers, polyethylene, polystyrene, polybutadiene, polydimethylsiloxane (PDMS), polypropylene, polymethylmethacrylate, polytetrafluoroethylene and polyvinyl chloride (PVC).

Additional examples of suitable polymers include, but are not limited to, those described in the references cited in this written description and incorporated by reference herein. Nomenclature pertinent to molecular structures, as well as description of monomers and side chain structures useful for the present invention can be found in U.S. Patent Publication No. U.S. 2009/0011946, which is hereby incorporated by reference in its entirety.

As used herein, the term "polysaccharides" refers to polymeric carbohydrate structures, formed of repeating units (either mono- or di-saccharides) joined together by glycosidic bonds. Polysaccharides of the invention are preferably linear, but may contain various degrees of branching. Additionally, polysaccharides are generally heterogeneous, containing slight modifications of the repeating unit. Examples of polysaccharides suitable for the invention include homopolysaccharides or homoglycans, where all of the monosaccharides in a polysaccharide are the same type, and heteropolysaccharies or heteroglycans, where more than one type of monosaccharide is present. In exemplary embodiments, the polysaccharide is a starch, glycogen, cellulose, or chitin.

Polysaccharides of the invention have the general formula of $C_x(H_2O)_y$. In some embodiments, X is about 100 to about 100,000, about 200 to about 10,000, about 500 to about 5,000, or about 1,000 to about 2,000. In another embodiment, polysaccharides have repeating units in the polymer backbone of about six-carbon monosaccharides and can be represented by the general formula of $(C_6H_{10}O_5)_n$ where n is about 30 to about 100,000, about 200 to about 10,000, about 500 to about 5,000, or about 1,000 to about 2,000.

As used herein, the terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA") or RNA/DNA hybrids. It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, siRNA, and mRNA, whether spliced or unspliced, any other type of polynucleotide which is an N- or C-glycoside of a purine or pyrimidine base, locked nucleic acids (LNA) which have one or more RNA nucleotides with a modified ribose that has an extra bridge connecting the 2' oxygen and 4' carbon (Petersen M. et al. Trends Biotechnol. 21 (2): 74-81 (2003)) and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic nucleic acid polymers providing that the polymers contain nucleobases in a configuration which allows for base pairing and base stacking, such as is found in DNA and RNA. The term nucleotides include hybrids thereof, for example between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine and psoralen), those containing chelates (e.g., metals, radioactive metals, boron, oxidative metals, etc.), those containing alkylators, those with modified linkages (e.g., alpha anomeric nucleic acids, etc.).

Oligonucleotides of defined sequences are used for a variety of purposes in the practice of the invention. Methods of making oligonucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

As used herein, the term "polypeptides" refers to a polymer formed from the linking, in a defined order, of preferably, α-amino acids, D-, L-amino acids and combinations thereof. The terms "peptides," "oligopeptides," and "proteins" are included within the definition of polypeptide. The term includes polypeptides containing post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide. The link between one amino acid residue and the next is referred to as an amide bond or a peptide bond. The terms do not refer to a specific length of the polypeptide.

In some embodiments, the elongated region of one or both probes comprise a non-biological hydrophilic polymer, such as polyethylene oxide (PEO), polyethylene glycol (PEG), polyisopropylacrylamide (PNIPAM), polyacrylamide (PAM), polyvinyl alcohol (PVA), polyethylenimine (PEI), polyacrylic acid, polymethacrylate and polyvinylpyrrolidone (PVP), or a combination thereof.

In preferred embodiments, the elongated region of one or both probes and/or the target analyte comprises a biomolecule, such as a polysaccharide, polynucleotide, or a polypeptide, or a combination thereof.

A preferred embodiment is a method of detecting a target analyte in a sample. In this method, a complex is provided, the complex formed from: a first probe coupled to a detectable piece and bound to said analyte if present, and a second probe coupled to a solid support and bound to said analyte if present, so that only if the target analyte is present in the sample, the detectable piece is directly or indirectly coupled to the solid support via a complex formed by the target analyte and the first and second probes, and wherein the complex optionally comprises an elongated region. It will be understood that the provided complex may have been formed in any possible manner and order of steps. It will also be clear that the person(s) who carries out any of the complex-formation steps may, but need not be, the person who performs the subsequent steps in the process, i.e., contacting the complex with a disruptor, applying force.

Preferably, the first probe, the second probe, and the target analyte comprise nucleic acids or oligonucleotides. More preferably, the first probe and second probe each comprise a region for binding the target analyte. The first probe couples to a detectable piece. The second probe couples to the solid support.

In preferred embodiments, if the target analyte is a nucleic acid, the nucleic acid target can form base pairs with unpaired nucleotides in the first probe and with unpaired nucleotides in the second probe. In an aspect of this embodiment, the first probe further comprises a region for coupling to the detectable piece. For example, the first probe can comprise nucleotides that do not pair with the target analyte, a protein, a peptide, an antigen covalently attached to the 5' or 3' end of a nucleic acid, or an amine group.

In another preferred aspect, the target analyte is not a nucleic acid. When the target analyte is not a nucleic acid, the first and second probes preferably comprise an antibody or an aptamer.

In preferred embodiments, the complexes are exposed to a disruptor. The disruptor is selected so that it preferentially uncouples detectable pieces that are coupled to the solid support via a target complex while detectable pieces which are coupled without the target complex are not affected. After exposing the complexes to the disruptor, a force may be applied to ensure that uncoupled beads leave their location. This force is preferentially viscous drag and is applied using solution flow. Several other types of forces are suitable, such as gravity, magnetic force and electric force. The number of detectable pieces that leave their initial location or the detectable region is quantified. This quantification can be made in several ways: counting the total number of detectable pieces before and after the application of the disruptor, identifying each individual detectable piece and counting the ones that remain attached/tethered after the application of the disruptor, collecting and counting the detectable pieces that leave the detectable region, measuring the intensity of a signal generated by the detectable pieces before and after the application of the disruptor wherein the signal correlates with the number of detectable pieces. In the latter case, the conversion to number of detectable pieces may not be done and the reported signal is just the difference between the intensity before and after the application of the disruptor. Examples of suitable signals for intensity measurements include: light intensity generated by fluorescent or color molecules, and electrical current induced in a solenoid by magnetic particles.

In one embodiment, the complex formed by the target analyte and the first and the second probe may comprise an elongated region. In a preferred embodiment, the elongated region of the complex formed by the target analyte and the first and the second probe comprises double-stranded DNA having a total length of more than about 300 base pairs, preferably ranging from about 500 base pairs to about 300,000 base pairs, for example, from about 3,000 base pairs to about 150,000 base pairs.

In a preferred aspect, the target analyte is a nucleic acid and the first and second probes bind to locations on the target that are at least 300 nucleotides from each other. According to this aspect the target can be either double or single stranded. When the target is single stranded, the force required to extend it is significantly higher than the force required to extend a double stranded nucleic acid (Current Opinion in Structural Biology 2000, 10:279; Nucleic Acids Research 2014 (42), 3:2064). The force required to extend the single stranded nucleic acid can be modified by changing solution properties, such as ionic strength and temperature, and/or adding a molecule that binds to the single strand.

When the target analyte is a nucleic acid molecule, exposure of the target analyte to the first and/or second probe is preferably conducted under high stringency conditions. High stringency conditions favor the hybridization of nucleic acid molecules which are perfectly complementary or substantially perfectly complementary to single stranded nucleic acids in the probe and make more unlikely the binding of targets which are not perfectly complementary or substantially perfectly complementary. After exposure of the target solution to the first and/or second probe, washing or exposing the probes to a medium with high stringency can remove non-perfectly complementary molecules as well. High stringency conditions occur at high temperature, low salt concentration and high pH. Also, the presence of certain chemicals, such as formamide, can increase the stringency of the solution. In an embodiment, exposure of the target to probes and washing, when performed, are conducted preferably at temperatures between 20° C. and 70° C., ionic strength between 0.01 M and 1 M, and pH between 7 and 8.

Some methods of this invention contain "exposing" steps where the probe(s), detectable pieces, and/or solid support are exposed to the sample or one another. These exposing steps can occur in any order, or even simultaneously. For example, in one embodiment, reactants are exposed in the following order: a) the first and second probe are exposed to the target analyte, b) the first probe which comprises a first end for coupling to the detectable piece is exposed to the detectable piece c) the second probe which comprises a first end for coupling to the solid support, is exposed to the solid support. If these steps are conducted under conditions that allow reactants to bind or couple and if the target analyte is present in the sample, the detectable piece is indirectly coupled to the solid support via a complex formed by the target, and the first and second probes. However, in another embodiment of the present invention, the steps are conducted in reverse order (c-b-a). If these steps are conducted under conditions that allow reactants to bind or couple and if the target analyte is present in the sample, the detectable piece is indirectly coupled to the solid support as before: via the first probe, the target analyte and the second probe. In another exemplary embodiment all the steps can be conducted simultaneously. If this single step is conducted under conditions that allow reactants to bind or couple and if the target analyte is present in the sample, the detectable piece is indirectly coupled to the solid support in the same manner as the previous two examples: via the first probe, the target analyte and the second probe. Any order and/or combination of steps that are conducted simultaneously will have the same result, if each step is conducted under conditions that allow reactants to bind or couple.

The methods of this invention can include one or more washing steps. A washing refers to an exchange of the solution that the solid support is in contact with. The washing can be used to apply a fluid drag force on the detectable pieces such that uncoupled detectable pieces are removed, and only the detectable pieces which are coupled (specifically and non-specifically) to the solid support are left on the solid support. A washing step can also be used to replace the buffer in contact with the solid support for a buffer of different stringency. For example, a high salt buffer (>0.1 Molar Sodium Chloride) may be exchanged for one of low salt (<0.1 Molar Sodium Chloride). High stringency buffers and/or fluid drag force can be used to denature complexes formed with analytes that are not the target but resemble the target analyte and therefore are capable of binding to the first and second probe.

In preferred embodiments, the detectable piece is a solid bead with a diameter between about 0.1 micrometer and about 20 micrometer, or between about 0.3 micrometer and about 5 micrometer. Preferred bead materials include: silica-based glasses, such as quartz and borosilicate; zirconium; and organic polymers, such as polystyrene, melamine resin and polyacrylonitrile.

In preferred embodiments, the detectable piece is a superparamagnetic bead with a diameter between about 0.3 micrometers and about 5 micrometers. Superparamagnetic beads are commonly used in biotechnological applications. They consist of a polymer matrix that contains small (less than about 10 nanometers) particles of a ferromagnetic material in it. The small size of the ferromagnetic particles makes them superparamagnetic. As a result, the beads are magnetic only under the influence of an external magnetic field.

In some embodiments, the detectable piece is a quantum dot. A quantum dot is typically less than about 10 nanometers and made of semiconductor materials that display quantum mechanical properties. As a result of these properties, the electronic characteristics of quantum dots are related to the size and shape of the individual crystal. Quantum dots are fluorescent and the emission frequency increases as the size of the quantum dot decreases. Therefore, the color of quantum dots can be controlled by their size.

In some embodiments, the detectable piece is a nanorod. Preferably, the length of the nanorods is at least about 0.5 micrometers. Methods of making nanorods or nanowires are known in the art. See for example, Hahm and Mieber, Nano Lett, 4, 51-54 (2004) (silicon nanorods); Li et al., Appl. Phys. Lett. 4, 4014-1016 (2003) (In2O3 nanorods); Liu et al., Phys. Ev. B. 58, 14681-14684 (1998) (Bismuth nanorods); Sun et al., Appl. Phys. Lett. 74, 2803 (1999) (Nickel nanorods); Ji et al., J. Electrochem. Soc. 150, C523-528 (2003) (Au/Ag multilayers and multisegment nanorods); Celedon et al., Nano Lett., 9, 1720-1725 (2009) (Pt/Ni multisegment nanorods); O'Brien et al., Adv. Mater. 18, 2379-2383 (2006) (polymer nanorods); Liu et al. Nanotechnology 20, 415703 (2009) (superparamagnetic and ferromagnetic Ni nanorods).

In some embodiments, the detectable piece comprises a fluorescent molecule. These molecules are known to those skilled in the art. For example, a fluorescent nucleic acid can be created in a PCR reaction where one of the deoxynucleotides in the reaction mix has a florescent label. A commonly used labeled deoxyadenosine triphosphate for this procedure is Fluorescein-12-dATP. Protocols to label nucleic acid molecules are readily available (Nucl. Acids Res. (1994) 22 (16):3418; Nat Biotechnol. (2008) 26(3):317; Nat Biotechnol. (2000) 18 (2):233). Another example of fluorescent molecule is a single fluorophore, such as Cy3 and other cyanines, and fluorescein.

In some embodiments, the detectable piece comprises an enzyme capable of catalyzing the formation of a detectable molecule. Examples of this type of enzyme include horseradish peroxidase and alkaline phosphatase. These enzymes act on numerous substrates, including chromogenic and chemiluminescent substrates. Horseradish peroxidase produces a coloured, fluorimetric, or luminescent derivative of the labeled molecule when incubated with a proper substrate, allowing it to be detected and quantified. Horseradish peroxidase catalyses the oxidation of luminol to 3-aminophthalate via several intermediates. The reaction is accompanied by emission of low-intensity light at 428 nm. An example of this embodiment is a detectable piece comprising a branched nucleic acid, which can contains several enzymes (Nucl. Acids Res. (1997) 25 (15): 2979)

In some embodiments, the probes and/or target may be labeled before or after the application of force with at least two detectable pieces, one detectable piece at one end of the probe-target complex, the other at the other end. In one embodiment, the elongated region of the complex may be labeled substantially along its length with fluorescent molecules. For example, the elongated region may be a double stranded DNA that is labeled with a nucleic acid fluorescent dye, such as YOYO-1. The approximate length of the elongated region can be determined from the position of said particles after the application of force. In these embodiments the discrimination of non-specific interaction is based on the length of the elongated region. If the full length of the elongated region is observed, it means that the target analyte is present. Instead, if a fraction of the length of the elongated region is observed, it means that the attachment to the solid support is via non-specific interactions.

In an aspect according to some of the embodiments, a force is applied to the detectable pieces. The force field acts on the detectable piece and pulls it away from its initial position (e.g. a magnetic field acting on a magnetic particle or a flow exerting a drag on a particle). The device is exposed to a sample in conditions such that if the target analyte is present, then a complex is formed by the target analyte and the first and second probes. Consequently, when a force is applied, the detectable piece that is associated with the complex will move a distance that is a function of the length of the complex.

In preferred embodiments, the presence of the target analyte in the sample is indicated by detectable pieces that: i) suffer a displacement within a pre-determined range and ii) leave their initial location after the complex is exposed to a disruptor. In these embodiments, the signal generated by non-specific interactions is reduced as shown in Example 1 and Example 2. The pre-determined displacement is given by the length of the complex elongated region. The requirement that pieces suffer a displacement within a range removes from consideration detectable pieces that are non-specifically attached and suffer a displacement that is different than expected based on the length of the elongated region, for example pieces that are directly attached to the solid support will move a distance that is less than the pre-determined range. However, some detectable pieces that are non-specifically attached suffer a displacement that is within the pre-determined range. This can happen when beads attach non-specifically to the elongated molecule (as exemplified by beads 202 and 302 in FIGS. 2A, 2B, and 3). The requirement that pieces leave their initial location removes from consideration most detectable pieces that are non-specifically attached. However, some detectable pieces that are non-specifically attached can leave their initial location. This can happen, for example, when the non-specific attachment is reversible. By combining requirements i) and ii), the signal generated by non-specifically attached pieces is greatly reduced.

In other embodiments, instead of applying a force and measuring the amount of the detectable piece displacement, the amount of Brownian motion in the absence of force is measured. The amount of Brownian motion of a detectable piece in the absence of force increases with the length of the tether that couples the detectable piece to the solid support and can be used to estimate the length of the tether. Therefore, Brownian motion can be used, for example, to discriminate detectable pieces that are non-specifically attached to the solid support from detectable pieces that are attached to the solid support via a complex that comprises an elongated molecule.

In one embodiment, the detection device is exposed to the sample in conditions such that the number of beads tethered by probes is proportional to the concentration of the target analyte. In this manner, the detectable signal is proportional to the concentration of the target analyte, thereby permitting the concentration of the target analyte in the sample to be determined.

Preferred embodiments use probes having elongated regions of multiple different lengths, with each probe of a certain length having a region capable of binding a specific target analyte, in such a manner that each probe length is associated with a different target analyte. In this embodiment, the approximate concentration of multiple target analytes in a sample can be determined in a single assay by measuring different displacements of particles after application of force, grouping them based on the amount of displacement and counting the number of particles associated with each possible displacement.

In related embodiments, the multiplexing capability is further increased by modifying the probes having elongated regions in such a manner that each of them may have more than one length and the change of length is triggered by an external agent. Examples of external agents that can trigger a change of length are temperature, ionic strength, pH, force, an auxiliary molecule, such as a nucleic acid, an enzyme a detergent, etc. In these embodiments, the identity of a target is determined after measuring the displacement of the detectable piece before and after triggering the change of length. The change of length can be triggered multiple times. For example, in an assay with 100 different probes having an elongated region, each probe specific to a different target analyte can be created by a set of probes that have 10 different lengths before triggering the length change and wherein each probe experiences one out of 10 possible different length changes upon triggering the length change. An example of a probe with an elongated region having a length that can be changed by an external agent is a probe in which two remote positions in the probe interact in such a manner that an internal loop is formed. In this case, the external agent can trigger the release or the formation of an internal loop. The characteristics of the external agent required to trigger the change of length are controlled by the characteristics of the interaction. For example, if the interaction is the hybridization between nucleic acid molecules, the specific sequence can be used to modulate the characteristics of the triggering agent. An example of an external agent that can trigger the release of an internal loop formed by hybridization between nucleic acid molecules is an auxiliary nucleic acid complementary to one of the molecules in the hybridization region that holds an internal loop. When the probe is exposed to this auxiliary nucleic acid, the auxiliary nucleic acid can displace one of the strands in the hybridization region, thereby releasing the loop. Another example of an external agent is an auxiliary nucleic acid that has a first and a second region, wherein the first region is complementary to a first region in a nucleic acid probe and the second region is complementary to a second region in the probe. When the probe is exposed to this nucleic acid, the nucleic acid binds to the two regions in the probe which produces an internal loop. In related embodiments, the auxiliary molecules are proteins that can be used similarly to the nucleic acid described above with the purpose of releasing or forming internal loops.

The surfaces and probes of the present invention may have a plurality of different analyte binding molecules attached to them, and as a result, the tethering of detectable pieces to the solid support could be triggered by a plurality of target analytes.

In one embodiment, a solid support may have an array of regions, each region comprising a second probe specific to a unique target analyte. Thus, exposure of the solid support to the sample captures different targets at different locations in the array. Therefore, detection of detectable piece displacement in a specific array region indicates that the corresponding target analyte is present in the sample. According to this embodiment, a method is provided for creating a unique profile or fingerprint of a sample having any number of different target analytes (e.g., any of two through one thousand, or even more). As such, profiles from different samples can be stored in a database and/or compared for diagnostic purposes for the detection of diseases or disorders.

Another embodiment uses multiple distinguishable particles, wherein each different detectable piece comprises a different first probe specific to a different molecule. For example, fluorescent beads of different colors are functionalized with different antibodies, one antibody kind for each bead color. In this manner, the specific target analytes present in the sample are identified by detecting the color of the tethered beads that are displaced under a force. Alternatively, beads of different sizes or distinguishable strings of fluorescent molecules or particles can be used (Nat. Biotech. 26, 317-325, 2008).

In a preferred aspect of some of the embodiments, the applied force is fluid drag. This type of force is generated by the flow of the liquid solution in which the detectable piece is immersed. More precisely, this force is applied when there is a difference between the speed of the liquid and the speed of the detectable piece. This force is often parallel to the solid support, but it can have a component perpendicular to the solid support if the solid support is porous. In preferred embodiments, the particles are in proximity to the surface of the solid support and the flow is substantially parallel to the surface of the solid support. In these embodiments, the speed of the fluid increases away from the surface of the solid support and not only produces a linear force substantially parallel to the surface of the solid support but also a torque. The terms "fluid drag" and "fluid drag force" are used to indicate the combination of both the linear force and torque, when it exists, experienced by the particles. In preferred embodiments, the particles have a diameter or length less than about 20 micrometers and the flow is laminar, with a Reynolds number less than about 1. Typically, the particles and/or molecule are inside a capillary tube and flow can be generated using a pump, such as a syringe pump, connected to the capillary by a hose. Another way of generating a suitable flow is to exert an external pressure on the hose connected to the capillary. The pressure moves a small amount of fluid into the capillary, which displaces the particles away from the side of the capillary where the pressure was applied. Releasing the pressure in the hose displaces the beads in the opposite direction.

In an aspect of some of the embodiments, the applied force on the detectable piece is fluid buoyancy. This type of force is equal to the weight of the fluid displaced by the detectable piece and in the direction opposite to the gravitational force.

In an aspect of some of the embodiments, the applied force is a magnetic force. In these embodiments, the particles are magnetic, such as superparamagnetic beads. The force is a consequence of the presence of a magnetic field which can be generated with permanent magnets, such as iron or rare earth magnets, or electromagnets. The magnetic force can be used to pull the particles away from the glass surface, in such a way that particles tethered via an elongated region are displaced to a plane higher than the particles non-specifically attached to the surface. This type of displacement can be detected optically using an imaging system able to image planes parallel to the solid support. In this imaging system, this type of displacement produces a change in diffraction pattern when the detectable piece moves to a different focal plane. Alternatively, the magnetic force can be used to pull the particles in a direction parallel to the surface of the solid support. This type of displacement is easily detected as a change of position of the particles in the image using an optical system.

In another aspect of some of the embodiments, the applied force is gravitational. In these embodiments the direction of the force is always toward the center of the earth and therefore its direction with respect to the solid support is determined by the orientation in space of the solid support.

In another aspect of some embodiments, the applied force is centrifugal. In these embodiments, the particles are subjected to a motion that changes direction. Preferably, the motion is a rotational motion.

In another aspect of some of the embodiments, the applied force is electrical. An electrical force is generated when at least two electrodes having different voltage are introduced in the solution generating a voltage gradient.

In another aspect of some of the embodiments, the force is applied to the target-probe complex using flow, a receding meniscus, or a voltage gradient.

In embodiments that use a force substantially parallel to the solid support, such as embodiments that apply fluid drag substantially parallel to the solid support, the force can remove non-specifically bound particles while not significantly reducing the signal because being part of a complex with an elongated region reduces the force experienced by the target analyte. When force substantially parallel to the solid support is applied on particles bound to the solid support, the tension on the tether decreases with tether length (Langmuir 1996, 12(9): 2271). Therefore, non-specific interactions, which are normally tethers about 10 nanometers long, experience tensions that are significantly higher than the tension that a target bound in an elongated complex experience. This property of long tethers allows in embodiments of the present invention the removal of non-specifically bound particles without significantly affecting specifically bound particles. Using complexes comprising an elongated region larger than the non-specific tethers present in a particular assay improves the selective removal of non-specifically bound particles in that assay. If the tethered detectable piece is a sphere of radius a touching the solid support that experiences a force parallel to the solid support, as shown in FIG. 8A, then the tension (T) in the tether (length L) as a function of the horizontal force (F) can be calculated by balancing forces and torques. FIG. 8B shows the value of the ratio of tension and horizontal force (T/F) as a function of the ratio of tether length and detectable piece radius (L/a). The tension in the tether dramatically increases for tether lengths that are less than half the radius of the particle. For example, for a tether that is 0.01 times the radius of the particle, the tension is 7 times higher than the horizontal force, while for a tether that is 2 times the radius of the particle, the tension is only 6% higher than the horizontal force. In embodiments that apply fluid drag substantially parallel to the solid support, the torque applied on the detectable piece by the drag further increases the difference in the tension experienced by short versus long tethers.

The application of force to the complex formed by the target analyte and the first and second probes either directly or indirectly through force applied to the detectable piece can increase the target specificity of the detection system by removing complexes where the target is not the exact binding partner of the binding regions in the probes. When the target is a nucleic acid, this situation takes place, in most cases, when the target is not perfectly complementary to a nucleic acid region in the probes. The application of force is a novel form of hybridization stringency. This stringency can be modulated by the configuration of the structure formed by probes when they bind to the target. In particular for nucleic acids, a probe can hybridize to a target in two main types of configurations. In a first configuration, the axis of the duplex is in the direction of the force and the application of force tends to disrupt all the base pairs simultaneously. In a second configuration, the axis of the duplex is perpendicular to the direction of the force and the application of force tends to disrupt base pair in a progressive order, starting with the ones closer to the point of force application. The stringency can be modulated by the amount of force applied (Current Opinion in Chemical Biology 2008, 12: 640, PNAS 2006 (103), 16:6190).

In some embodiments, the present invention may be incorporated into an assay as described in: International Patent Publication WO 2013/059044; United States Patent Application Publication US 2014/0099635 A1; United States Patent Application Publication US 2016/0258003 A1; and United States Patent application Publication US 2015/0307926 A1; the contents of these publications are incorporated by reference herein.

In some embodiments of the present invention, the presence and displacement of the particles is detected using an imaging system, wherein the imaging system generates an image of the particles and/or the probes-target complex that is detected by a sensing device. The image can be a regular image or a transformed representation of the object such as a shadow. The imaging system consists of four main components: illumination, specimen, image forming part, and a detector, which are sequentially positioned on the spatial path. An example of an imaging system is the optical microscope, and in this case the image forming part is the lens/lenses. Optical microscopes are well known by those of skill in the art. Optical microscopes can visualize unstained samples using image contrast of scattering, absorption or phase contrast, or stained samples with fluorescence or other scheme of light emission. The light source employed in a microscope can be coherence light source (such as laser) or incoherent source (such as LED or white light source). The lenses of a microscope can be a single lens, a series of lenses, or a compound lens which is usually called an objective. A macroscope is another example of imaging system. The main difference between a macroscope and microscope is the lens/objective they use. The microscope lens usually has magnification equal or larger than 1×, meaning the size of image is larger than the object. That results in a small field of view. The macroscope lens can have magnification smaller than 1×, which allows for visualization of a large area. A lens-free imaging system is another example of an imaging system. This type of system uses a digital optoelectronic sensor array, such as a charged coupled device (CCD) or a CMOS chip to directly sample the light transmitted through a specimen without the use of imaging lenses between the object and the sensor plane (Greenbaum, Nat. Methods 2012, 9, 9, 889-895; Gurkan, U. A., et al., Biotechnol. J. 2011, 6, 138-149). The lensless ultra wide-field cell monitoring array platform (LUCAS) (Ozcan, A. and Demirci, U. Lab Chip, 2008, 8, 98-106) is an example of this type of microscopes. The LUCAS platform is based on recording the "shadow images" of microscopic objects onto a sensor array plane. Microscopic objects are uniformly illuminated with an incoherent light source or a laser. The cell shadow pattern is digitally recorded using a CCD or CMOS sensor array. A coherent imaging system is another example of image system. This type of system uses the object to modulate the illumination laser beam and makes the modulated beam interfere with a reference laser beam or the same illumination beam, then the interferential information is recorded to reconstruct the information of the object. Digital holography (Javidi, Opt. Lett., 2000, 25, 9, 610-612) and in-line holography (Xu, PNAS, 2001, 98, 20, 11301-11305) are examples of this technique.

In some embodiments, the displacement of the magnetic particles is detected from the induced current in a solenoid.

The present invention also is directed to a kit for detecting a target analyte in a sample, the kit comprising a) a particle; and b) a first probe capable of binding to the analyte, and to either a solid support or to the particle, the first probe optionally comprising an elongated region that is longer than about 0.1 micrometers, preferably between about 0.3 and about 100 micrometers long; c) a disruptor molecule, d) packaging material; and optionally e) instructions for use. In a particular embodiment, the kit may further comprise a second probe capable of binding to the analyte at a location different than the location that the first probe binds to the analyte, and which also is capable of binding to either a solid support or to the particle. The second probe may optionally contain an elongated region that is longer than about 0.1 micrometers, more preferably between about 0.3 and about 100 micrometers long. If the first probe is for coupling to a solid support, the second probe is for coupling to the particle, and if the first probe is for coupling to the particle, the second probe is for coupling to the solid support. The packaging material would be known to one of ordinary skill, and in certain embodiments would include conventional bottles, vials, boxes, etc. The optional instructions for use would preferably include conventional printed materials included within the packaging material.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Example 1

This example demonstrates detection of 4 CFU of *Candida albicans*. The reagents used are listed here with reference to FIG. 3: a first probe (304) is a DNA oligonucleotide with a first region of 26 nucleotides (nt) having a sequence complementary to a region of rRNA in the small ribosomal subunit of *C. albicans*, a second region with a random 20-nt sequence that is a toehold for a strand-displacement molecule, and a 25-nt poly A region (only adenine bases); 1-micron superparamagnetic beads (301, 302, 303) functionalized with a 30 nt poly T oligonucleotide (only thymine bases) (305), note that only one oligonucleotide is shown on the surface of the bead, but in reality the surface of the bead is covered with many oligonucleotides; a second probe (307) generated as described below and a glass capillary (50 mm×4 mm×0.2 mm) functionalized with a 36-nt single stranded DNA oligonucleotide with a random sequence (310). The second probe was generated in the following manner: A plasmid (5.4 kbps) was linearized using the restriction enzyme, which cut the plasmid twice generating a large fragment with different 4 nt overhangs at each end, and a small fragment which was separated and discarded. The linearized plasmid was ligated using T4 ligase to two double stranded DNA fragments generated by hybridizing synthetic oligonucleotides. The first fragment had one end with an overhang compatible to one of the overhangs of the plasmid and the other end had a 26-nt overhang complementary to a region of the *C. albicans* rRNA in the small ribosomal subunit different from the region where the first probe binds. The second fragment had one end with an overhang compatible to the other overhang of the plasmid, and the other end had a 36-nt overhang complementary to the capture probe (309). A solution containing 1 CFU of *C. albicans* per microliter was lysed by heating to 90° C. for 8 minutes. This lysate was used to spike a 50 microliter reaction that contained the first and the second probes with an equivalent of 4 CFU. The mixture was incubated at 65° C. for 30 minutes. Then, beads were added, and the mixture was incubated at 50° C. for 10 minutes. The mixture was then flowed into a glass capillary and beads were let sediment for 15 minutes. Buffer solution was flowed to wash unbound beads. The beads that remained attached to the bottom of the capillary were imaged with flow in one direction (first image) and then imaged again after the flow was reversed (second image). The optical system used to image the beads was composed of a LED ring light, a telecentric lens and a camera. The LED ring light provided a dark field illumination. The telecentric lens, which is popularly employed in machine vision, exhibited the same magnification for objects at different distances. The lens had a large depth of field of around 500 micrometers. The magnification of the system was 1:1, which helped to achieve a large field of view of 6.14 mm by 4.6 mm. According to the optical resolution of the lens, the image size of each particle was about 4 micrometers, which was sufficient to investigate the displacement of the particles. The camera used in the system had a 1/2.3 inch complementary metal oxide semiconductor (CMOS) chip, which had 4384 by 3288 pixels with pixel size of 1.4 micrometer.

A custom code written in Matlab was used to analyze the images and determine the displacement of most of the beads present in the field of view. Beads that were too close to each other (less than about 6 micrometers) were not included in the analysis. Comparing the position of each bead in the first and second images allowed measuring the displacement of over 5,000 beads in each experiment with sub-micrometer resolution. The displacement of all the beads in the field of view was used to generate a histogram of bead displacement. FIG. 4A shows the histograms obtained in two experiments, one with 4 CFU of cells in the reaction (top) and one without cells (bottom). The histograms show 3 peaks. Note that the peaks in the top histogram are displaced with respect to the peaks in the bottom histogram, however the distance between peaks is the same. The peaks close to zero displacement (405) and (406) correspond to beads that do not move and are non-specifically attached to the solid support, as shown in FIG. 3 (301). The peaks at about 3 microns (401) and (403) are generated by beads that are coupled to the solid support via a positive control molecule. The peak at about 4.5 microns (beads that suffer a displacement between 4.3 and 5.2 microns) is generated by beads that are coupled to the solid support via a complex formed by first probe, the target and the second probe. The beads that are non-specifically attached to the solid support with a small tether (309) and peak (405) can be easily discriminated from the beads in peak (402). Peak 402 has 3636 beads. However, the no-target experiment shows that not all the beads in (402) are coupled to the solid support via a target complex. In fact, the region (404) contains 807 beads (FIG. 4B). These beads are attached non-specifically at the end region of the second probe (302). The signal-to-background ratio is 3636/807≈4.5. We used the present invention to discriminate beads coupled via a target complex from beads that despite presenting a similar displacement are non-specifically attached to the second probe. A strand-displacement DNA oligonucleotide (377) was flowed into the capillary at 5 micro-Molar concentration. After 4 minutes of gentle flow another image was taken. The vicinity of the location of each of the 3636 beads that formed peak 402 was analyzed in the new image to detect which beads remained at the location and which beads had left the location. We found that 2860 beads had left in the experiment at 4 CFU. We found also that only 3 beads left in the experiment with no target. The signal-to-background ratio is 2860/3≈953. Therefore, the signal-to-background ratio was significantly improved by using the strand-displacement DNA oligonucleotide.

Example 2

Figures 5A, 5B:
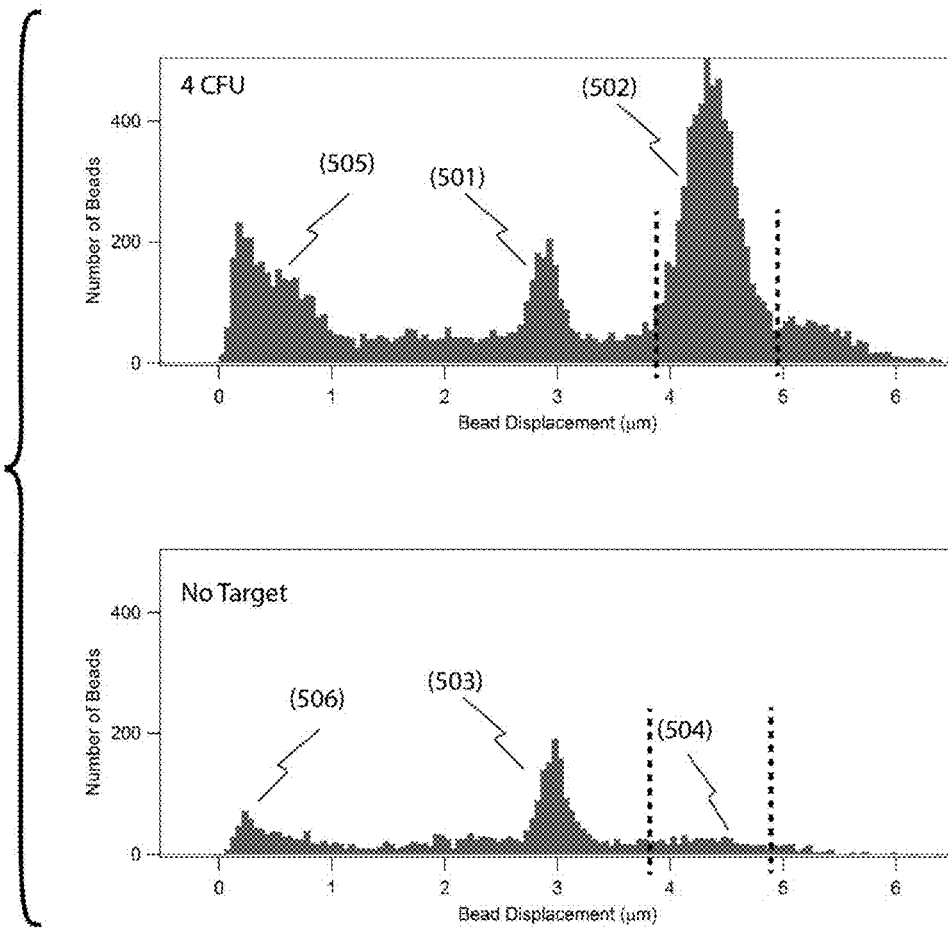
FIG. 5A and FIG. 5B show the results of the experiment described in Example 2.
Figure 6:
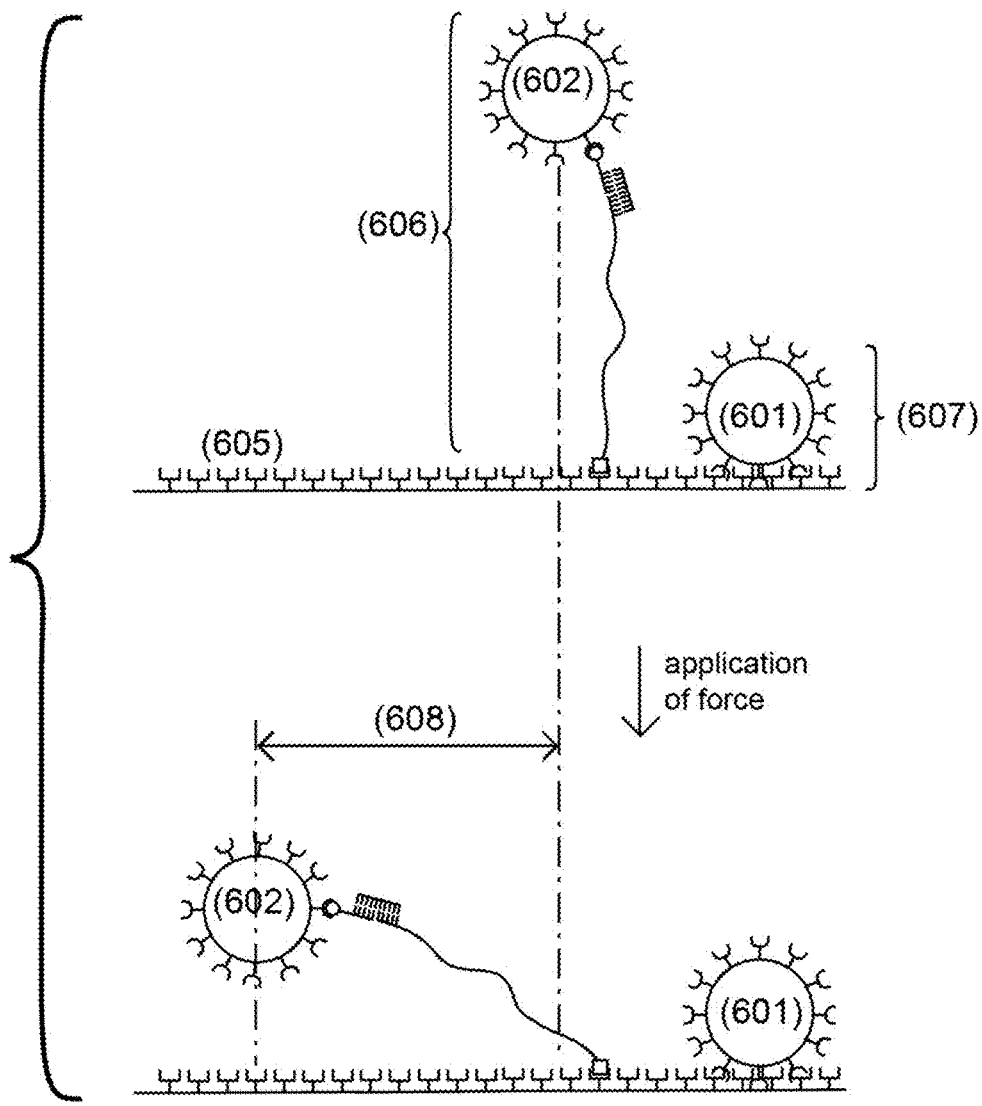
FIG. 6 depicts the effect of the application of force on particles attached to a solid support. If a particle (602) is attached to the solid support via a complex that comprises an elongated region (as shown at (606)), the particle moves a distance (608) that is a function of the length of the tether. If the particle (601) is non-specifically bound to the solid surface (as shown at (607)), the particle does not move or moves a distance significantly less than the specifically-bound particle (602).

In another example of the present invention, an experiment with the same reagents as in Example 1 was conducted. The protocol was also the same as in Example 1. The only difference was that instead of using a strand-displacement molecule as the disruptor, a degradation molecule was used (10), specifically, an RNase enzyme was used. FIG. 5A shows histograms obtained in these experiments and the table of FIG. 5B summarizes the total number of beads in peaks (502) and peak (504), as well as the number of beads from these peaks that left their location after exposure to RNase. Before disruption, the experiment with 4 CFU had 5549 beads that displaced the expected distance (502), while in the "no-target" experiment had 427 beads that displaced the expected distance (503). Therefore, the signal-to-background ratio was 5549/427≈13. The enzyme was flowed after obtaining the second image. Buffer with the enzyme was flowed at 0.5 gram per litter into the capillary and incubated for 10 minutes, after 4 minutes of gently flow another image was taken. As in Example 1, the vicinity of the location of each bead in peak (502) of FIG. 5A was analyzed in this new image and the number of beads that left their location was determined. We found that 4658 beads had left in the experiment at 4 CFU. We found also that only 15 beads left in the experiment with no target. The signal-to-background ratio is 4658/15≈310. Therefore, the signal-to-background ratio was significantly improved by using the RNase disruptor molecule.

Example 3

A 60 nucleotide (nt) synthetic RNA oligonucleotide target can be detected using a first probe consisting of 30 nt single stranded oligonucleotide having a sequence complementary to the 3' end of the target and a 30 nt poly A region (only adenine bases), 1-micron superparamagnetic beads functionalized with a 30 nt poly T oligonucleotide (only thymine bases), a second probe consisting of 30 nt single stranded oligonucleotide having a sequence complementary to the 5' end of the target and a 30 nt region with a sequence S1 and a glass capillary functionalized with a DNA oligonucleotide with a sequence complementary to S1. The first and second probes are mixed with a solution containing the target at 65° C. for 10 minutes. Then, the beads are incubated at 50° C. for 10 minutes. The mixture is then flowed into a glass capillary (50 mm×4 mm×0.2 mm) and let sediment. A buffer solution is flowed to wash unbound beads. A first image is taken and the beads that remained attached to the bottom of the capillary are counted or estimated using an image analysis algorithm. A disruptor RNase molecule in buffer at 0.5 gram per litter is flowed into the capillary and incubated for 10 minutes. Buffer is flowed to removed uncoupled beads. A second image is taken and the beads that remained attached to the bottom of the capillary are counted or estimated using an image analysis algorithm. The beads that leave the capillary after the incubation with the disruptor molecule are the relevant signal. To obtain this signal, the number of beads in the second image is subtracted from the number of beads in the first image.

Example 4

ELISA (enzyme-linked immunosorbent assay) is a plate-based assay technique designed for detecting and quantifying substances such as peptides, proteins, antibodies and hormones. Other names, such as enzyme immunoassay (EIA), are also used to describe the same technology. In an ELISA, an antigen must be immobilized on a solid surface and then complexed with an antibody that is linked to an enzyme. Detection is accomplished by assessing the conjugated enzyme activity via incubation with a substrate to produce a measurable product. ELISAs are typically performed in 96-well (or 384-well) polystyrene plates, which passively bind antibodies and proteins. It is this binding and immobilization of reagents that makes ELISAs so easy to design and perform. Having the reactants of the ELISA immobilized to the microplate surface makes it easy to separate bound from non-bound material during the assay. This ability to wash away nonspecifically bound materials makes the ELISA a powerful tool for measuring specific analytes within a crude preparation. A detection enzyme or other tag can be linked directly to the primary antibody or introduced through a secondary antibody that recognizes the primary antibody. It can also be linked to a protein such as streptavidin if the primary antibody is biotin labeled. The most commonly used enzyme labels are horseradish peroxidase (HRP) and alkaline phosphatase (AP). Other enzymes have been used as well, but they have not gained widespread acceptance because of limited substrate options. These include β-galactosidase, acetylcholinesterase and catalase. A large selection of substrates is available for performing ELISA with an HRP or AP conjugate. The choice of substrate depends upon the required assay sensitivity and the instrumentation available for signal-detection (spectrophotometer, fluorometer or luminometer). ELISAs can be performed with a number of modifications to the basic procedure. The key step, immobilization of the antigen of interest, can be accomplished by direct adsorption to the assay plate or indirectly via a capture antibody that has been attached to the plate. The antigen is then detected either directly (labeled primary antibody) or indirectly (labeled secondary antibody). The most powerful ELISA assay format is the sandwich assay. This type of capture assay is called a "sandwich" assay because the analyte to be measured is bound between two primary antibodies—the capture antibody and the detection antibody. The sandwich format is used because it is sensitive and robust.

No matter the type of ELISA assay performed, non-specific interactions result in the coupling of enzymes to the solid support that is not mediated by target molecule which generates background noise. This background noise reduces the sensitivity of the assay. According to the present invention, the background can be substantially eliminated by exposing the solid support to a disruptor which preferentially uncouples enzymes molecules coupled via a target complex and then measuring the signal intensity that is generated by the enzymes that leave their initial location. Alternatively, after exposing the solid support to a disruptor, the solid support can be washed, and the signal generated by enzymes that remain on the surface is measured to determine the background noise which can be subtracted to the initial signal intensity to determine the real signal.

Example 5

A standard branched DNA assay begins with a solid support functionalized with single stranded DNA molecules known as capture DNA. Next, an extender DNA molecule is added. Each extender has two domains; one that hybridizes to the capture DNA molecule and one that is capable of binding to the target. Once the capture and extender molecules are in place and they have hybridized, the sample can be added. Target molecules in the sample will bind to the extender molecule. This results in a base peppered with capture oligonucleotides, which are hybridized to extender probes, which in turn are hybridized to target molecules. At this point, signal amplification takes place. A label extender DNA molecule is added that has two domains (similar to the first extender). The label extender hybridizes to the target and to a pre-amplified molecule. The preamplifier molecule has two domains. First, it binds to the label extender and second, it binds to the amplifier molecule. An example amplifier molecule is an oligonucleotide bound to the enzyme alkaline phosphatase.

Non-specific interactions result in the coupling of amplifier molecules to the solid support that is not mediated by target molecule which generates background noise. This background noise reduces the sensitivity of the assay. According to the present invention, the background can be substantially eliminated by exposing the solid support to a disruptor which preferentially uncouples amplifier molecules coupled via a target complex and then measuring the signal intensity of the amplifiers that leave their initial location. Alternatively, after exposing the solid support to a disruptor, the solid support can be washed, and the signal generated by amplifiers that remain on the surface is measured to determine the background noise which can be subtracted to the initial signal intensity to determine the real signal.

Example 6

Lateral flow tests also known as lateral flow immunochromatographic assays, are simple paper-based devices intended to detect the presence (or absence) of a target analyte in liquid sample (matrix) without the need for specialized and costly equipment, though many lab based applications exist that are supported by reading equipment. Typically, these tests are used for medical diagnostics either for home testing, point of care testing, or laboratory use. A widely spread and well-known application is the home pregnancy test. The technology is based on a series of capillary beds, such as pieces of porous paper, microstructured polymer, or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. In principle, any colored particle can be used, however latex (blue color) or nanometer sized particles of gold (red color) are most commonly used. The gold particles are red in color due to localized surface plasmon resonance. Fluorescent or magnetic labeled particles can also be used, these require the use of an electronic reader to assess the test result. Lateral Flow Tests can operate as either competitive or sandwich assays. In sandwich assays, as the sample migrates along the assay, it first encounters a conjugate, usually colloidal gold, which is labelled with antibodies specific to the target analyte. If the target analyte is detected within the sample the conjugate antibodies will bind and subsequently reach the test line which also contains antibodies specific to the target. Once the sample reaches the test line and the target analyte is present a visual change, normally a line appearing, will occur allowing the test to be read as a positive. Most sandwich assays also have a control line which will appear regardless of whether or not the target analyte is present. The rapid, low-cost sandwich-based assay is commonly used for home pregnancy tests which detects for human chorionic gonadotropin, hCG, in the urine of women.

In competitive assays, the sample first encounters colored particles which are labelled with the target analyte or an analogue. The test line contains antibodies to the target/its analogue. Unlabeled analyte in the sample will block the binding sites on the antibodies preventing uptake of the colored particles. The test line will show as a colored band in negative samples.

In both sandwich and competitive lateral flow assays, non-specific interactions result in the coupling of particles to the solid support that is not mediated by target molecule which generates background noise. This background noise reduces the sensitivity of the assay. According to the present invention, the background can be substantially eliminated by exposing the solid support to a disruptor which preferentially uncouples particles coupled via a target complex and then detecting/measuring the particles that leave their initial location. Alternatively, after exposing the solid support to a disruptor, the solid support can be washed, and the particles that remain on the surface are detected/measured to determine the background noise which can be subtracted to the initial signal intensity to determine the real signal.

Example 7

A DNA microarray (also commonly known as DNA chip or biochip) is a collection of microscopic DNA spots attached to a solid surface. DNA microarrays can be used to measure the expression levels of large numbers of genes simultaneously or to genotype multiple regions of a genome. Each DNA spot can contain as little as 1 picomole ($10^{-12}$ moles) of a specific immobilized DNA oligonucleotide (capture oligonucleotide). These can be a short section of a gene or other DNA element that are used to hybridize a cDNA or cRNA (also called anti-sense RNA) in a sample (target) under high-stringency conditions. Probe-target hybridization is usually detected and quantified by detection of fluorophore-, silver-, or chemiluminescence-labeled targets to determine relative abundance of nucleic acid sequences in the target.

Labeled nucleic acids in the sample that are not complementary to the capture oligonucleotides in a spot couple to the solid support at that spot via non-specific interactions which generates background noise. This background noise reduces the sensitivity of the assay. According to the present invention, the background can be substantially eliminated by exposing the solid support to a disruptor which preferentially uncouples labeled nucleic acids coupled via a target complex and then detecting/measuring the labeled nucleic acids that leave their initial location. Alternatively, after exposing the solid support to a disruptor, the solid support can be washed, and the labeled nucleic acids that remain on the surface are detected/measured to determine the background noise which can be subtracted to the initial signal intensity to determine the real signal.

What is claimed is:

1. A method of detecting a target analyte in a sample, the method comprising:
   a) providing at least one detectable piece coupled to a solid support via a complex formed by the target analyte and a first and a second probe, wherein:
      i) the first probe is coupled to the detectable piece and bound to said analyte if present, and
      ii) the second probe is coupled to the solid support and bound to said analyte if present, so that only if the target analyte is present in the sample, the detectable piece is directly or indirectly coupled to the solid support at an initial location via the complex, wherein the complex comprises an elongated region that is at least 100 nanometers in length;
   b) either applying a force to the detectable piece and measuring the displacement of the detectable piece or measuring the amount of Brownian motion of the detectable piece;
   c) exposing the complex to a disruptor that is capable of uncoupling the detectable piece from the solid support, wherein the disruptor comprises a nucleic acid that can hybridize to the target analyte in a region where the target analyte hybridizes to the first or second probe and can hybridize to a toehold region in the target analyte which does not hybridize to the first or second probe, or
   wherein the disruptor comprises a nucleic acid that can hybridize to the first or second probe in a region where the first or second probe hybridizes to the target analyte and can hybridize to a toehold region in the first or second probe which does not hybridize to the target analyte;
   d) optionally applying a force to the detectable piece; and
   e) detecting if the detectable piece has left its initial location;
   wherein the presence of the target in the sample is indicated by detectable pieces that: i) suffer a displacement or Brownian motion within a pre-determined range and ii) leave their initial location.

2. The method of claim 1, further comprising the step of estimating the concentration of the target analyte based on the number of detectable pieces that leave their initial location.

3. The method of claim 1, wherein the first probe comprises a first nucleic acid that binds to a first region of the target analyte and the second probe comprises a second nucleic acid that binds to a second region of the target analyte.

4. The method of claim 3, which further comprises controlling the temperature of the sample to produce denaturation of double stranded nucleic acids in the sample and/or specific hybridization of nucleic acids in the sample to the first and second probes.

5. The method of claim 3, wherein the sample is initially treated with an exonuclease enzyme to convert double stranded nucleic acids into single stranded nucleic acids.

6. The method of claim 1, wherein the first probe comprises a first antibody or a first aptamer that binds to a first region of the target analyte and the second probe comprises a second antibody or second aptamer that binds to a second region of the target analyte.

7. The method of claim 1, wherein two or more different target analytes are detected by using a different combination of first and second probe for each target analyte, wherein each target forms a different target complex with the probes that bind to it, and wherein a disruptor disrupts the target complex of one or more target analytes.

8. The method of claim 7, wherein two or more different disruptors are sequentially contacted with the complexes and the detectable pieces that leave their initial location are quantified after each disruptor is contacted with the complexes.

9. The method of claim 1, which further comprises the step of coupling the first probe to the detectable piece.

10. The method of claim 1, which further comprises the step of coupling the second probe to the solid support.

11. The method of claim 1, which further comprises the steps of exposing the sample to the first probe and exposing the sample to the second probe.

12. The method of claim 11, wherein the further steps are performed in either order, or simultaneously.

13. The method of claim 12, which further comprises a step of exposing the sample to a detectable piece.

14. The method of claim 13, further comprising a washing step after one or more of the steps.

15. The method of claim 14, further comprising a lysing step.

16. The method of claim 1, wherein the force applied to the detectable piece comprises a magnetic force, a fluid drag force, an electrical force or a centrifugal force.

17. The method of claim 1, wherein the detectable piece comprises a particle.

18. The method of claim 17, wherein the particle is magnetic.

19. The method of claim 18, wherein the magnetic detectable piece is superparamagnetic.

20. The method of claim 1, wherein the detectable piece is fluorescent.

21. The method of claim 1, wherein the detectable piece is detected using an imaging system with a lens, with a lens-free microscope, or with a coherent imaging technique.

* * * * *